US007049421B2

US 7,049,421 B2
*May 23, 2006

(12) United States Patent
Hohn et al.

(10) Patent No.:
(45) Date of Patent:

(54) TRICHOTHECENE-RESISTANT TRANSGENIC PLANTS

(75) Inventors: Thomas M. Hohn, Chapel Hill, NC (US); Cheryl Peters, Raleigh, NC (US); John Salmeron, Hillsborough, NC (US)

(73) Assignee: Syngenta Participations AG, Schwarzwaldallee (CH)

( * ) Notice: Subject to any disclaimer, the term of this patent is extended or adjusted under 35 U.S.C. 154(b) by 125 days.

This patent is subject to a terminal disclaimer.

(21) Appl. No.: 10/614,954

(22) Filed: Jul. 7, 2003

(65) Prior Publication Data

US 2004/0034884 A1    Feb. 19, 2004

Related U.S. Application Data

(63) Continuation of application No. 10/074,279, filed on Feb. 12, 2002, now Pat. No. 6,646,184, which is a continuation of application No. 09/538,414, filed on Mar. 29, 2000, now Pat. No. 6,346,655.

(60) Provisional application No. 60/287,549, filed on Feb. 11, 2000, provisional application No. 60/304,177, filed on Mar. 31, 1999.

(51) Int. Cl.
*C12N 15/09* (2006.01)
*C12N 15/31* (2006.01)
*A01H 5/00* (2006.01)

(52) U.S. Cl. .................. 536/23.2; 536/23.7; 435/320.1
(58) Field of Classification Search ............... 536/23.2, 536/23.7; 435/320.1, 69.1
See application file for complete search history.

(56) References Cited

U.S. PATENT DOCUMENTS

| 5,773,696 A | 6/1998 | Liang et al. ................. 800/205 |
| 6,060,646 A | 5/2000 | Harris et al. ................. 800/301 |
| 6,346,655 B1 * | 2/2002 | Hohn et al. .................. 800/279 |

FOREIGN PATENT DOCUMENTS

| JP | 2000-32985 | 2/2000 |
| WO | WO 99 02703 | 1/1999 |
| WO | WO 99 09173 | 2/1999 |
| WO | WO 00 20573 | 4/2000 |

OTHER PUBLICATIONS

Bennetzen, J.L. and Jones, D.G., *Approaches and Progress in the Molecular Cloning of Plant Disease Resistance Genes Genetic Engineering*, vol. 14, (1992) pp. 99-124.
Desjardins et al., *Reduced Virulence of Trichothecene-Nonproducing Mutants of Gibberella zeae in Wheat Field Tests Molecular Plant-Microbe Interactions*, vol. 9, No. 9 (1996), pp. 775-781.
Harris et al., *Possible Role of Trichothecene Mycotoxins in Virulence of Fusarium graminearum on Maize Plant Disease*, vol. 83, No. 10 (1999) pp. 954-960.
Hohn et al., *Function and Biosynthesis of Trichothecenes Produced by Fusarium Species;* Proceedings of the 3$^{rd}$ Tottori International Symposium on Host-Specific Toxins, Daisen, Tottori, Japan, Published by Kluwer Academic, Dordrecht/Boston, #8258, pp. 17-24 (1998).
Hohn et al., Abstract Published for National Fusarium Head Blight Forum—St. Paul, Minnesota (Nov. 10, 1997).
Hohn, et al., Abstract Published for Symposium on HSTs—Tottori, Japan (Aug. 24, 1997).
Kimura et al., *Features of Tri101, the Trichothecene 3-0-Acetyltransferase Gene, Related to the Self-defense Mechanism in Fusarium graminearum Bioscience Biotechnology and Biochemistry*, vol. 62(5), (1998) pp. 1033-1036.
Kimura et al., *The Mystery of the Trichothecene 3-0-acetyltransferase gene; Analysis of the Region Around Tri101 and Characterization of its Homologue from Fusarium Sporotrichioides Federation of European Biochemical Societies Letters*, 435, (1998) pp. 163-168.
Kimura et al., *Trichothecene 3-0-Acetyltransferase Protects Both the Producing Organism and Transformed Yeast from Related Mycotoxins The Journal of Biological Chemistry*, vol. 273, No. 3 (Jan. 16, 1998) pp. 1654-1661.
Kim et al., *Ribosomal Protein Gene Expression and Trichothecene Resistance in Arabidopsis Thaliana* Ph.D. Dissertation, Ohio State University, 1991, Database Dissabs an 91:4157.
Linthorst et al., *Constitutive Expression of Pathogenesis-Related Proteins PR-1, GRP, and PR-S in Tobacco Has No Effect on Virus Infection The Plant Cell*, vol. 1 (Mar. 1989) pp. 285-291.
McCormick et al., *Disruption of TRI101, the Gene Encoding Trichothecene 3-0-Acetyltransferase, from Fusarium sporotrichioides Applied and Environmental Microbiology*, vol. 65, No. 12 (Dec. 1999), pp. 5252-5256.
Proctor et al., *Reduced Virulence of Gibberella zeae Caused by Disruption of a Trichothecene Toxin Biosynthetic Gene Molecular Plant-Microbe Interactions*, vol. 8, No. 4 (1995) pp. 593-601.
English abstract of JP200032985, dated Feb. 2, 2000.
Letter from USDA (Thomas Hohn) to Novartis Biotechnology (Bernard Vernooij), dated Mar. 24, 1998.

(Continued)

*Primary Examiner*—Medina A. Ibrahim
(74) *Attorney, Agent, or Firm*—Syngenta Participations AG

(57) ABSTRACT

The present invention discloses isolated polynucleotides encoding polypeptides having trichothecene 3-O-acetyltransferase activity, recombinant vectors and host cell comprising said polynucleotides.

5 Claims, 1 Drawing Sheet

OTHER PUBLICATIONS

O'Donnell et al., (2000) Gene genealogies reveal global phylogeographic structure and reproductive isolation among lineages of *Fusarium graminerum,* the fungus causing wheat scab. Proc. Natl. Acad. Sci. 97(14):7905-7910.

* cited by examiner

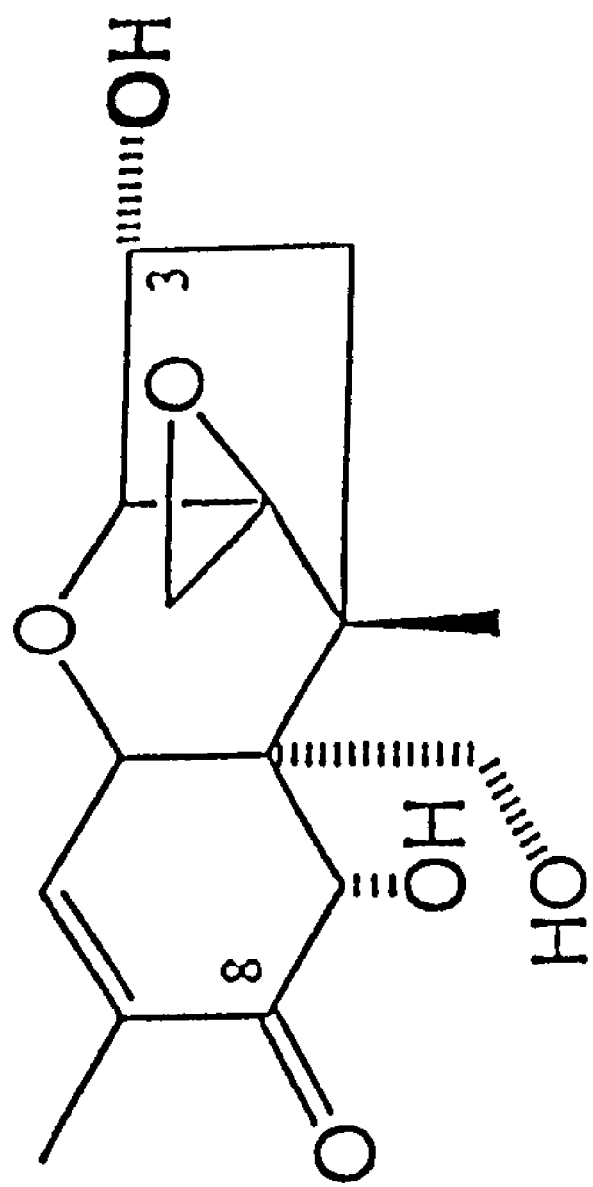
Fig. 1 Deoxynivalenol

TRICHOTHECENE-RESISTANT TRANSGENIC PLANTS

This application is a continuation of U.S. application Ser. No. 10/074,279, filed Feb. 12, 2002, now U.S. Pat. No. 6,646,184, which is a continuation of U.S. application Ser. No. 09/538,414, filed Mar. 29, 2000, now U.S. Pat. No. 6,346,655, which claims the benefit of U.S. Provisional Application No. 60/304,177, filed Mar. 31, 1999, and U.S. Provisional Application No. 60/287,549, filed Feb. 11, 2000, all of which are incorporated herein by reference in their entirety.

A) SUBJECT MATTER OF THE INVENTION

The present invention relates to transgenic hosts particularly transgenic plants, plant tissues, seeds and cells that are trichothecene resistant and methods of making and using the same. The present invention further relates to methods of preventing and/or reducing fungal growth on a plant, plant tissue, seed or plant cell. The present invention further relates to preventing and/or reducing mycotoxin contamination of a plant, plant tissue or seed. The present invention further relates to using trichothecenes as selective agents in transformation protocols.

B) BACKGROUND

Numerous fungi are serious pests of economically important agricultural crops. Further, crop contamination by fungal toxins is a major problem for agriculture throughout the world. Mycotoxins are toxic fungal metabolites, often found in agricultural products that are characterized by their ability to cause health problems for vertebrates. Trichothecenes are sesquiterpene epoxide mycotoxins produced by species of *Fusarium*, *Trichothecium*, and *Myrothecium* that act as potent inhibitors of eukaryotic protein synthesis. *Fusarium* species that produce such trichothecenes include *F. acuminatum*, *F. crookwellense*, *F. culmorum*, *F. equiseti*, *F. graminearum* (*Gibberella zeae*), *F. lateritium*, *F. poae*, *F. sambucinum* (*G. pulicaris*), and *F. sporotrichioides* (Marasas, W. F. O., Nelson, P. E., and Toussoun, T. A. 1984).

As previously described (A. E. Desjardins and T. M Hohn, Mycotoxins in plant pathogenesis. Mol. Plant-Microbe Interact. 10 (2):147–152, 1997), both acute and chronic mycotoxicoses in farm animals and in humans have been associated with consumption of wheat, rye, barley, oats, rice and maize contaminated with *Fusarium* species that produce trichothecene mycotoxins. Experiments with chemically pure trichothecenes at low dosage levels have reproduced many of the features observed in moldy-grain toxicoses in animals, including anemia and immunosuppression, hemorrage, emesis and feed refusal. Historical and epidemiological data from human populations indicate an association between certain disease epidemics and consumption of grain infected with *Fusarium* species that produce trichothecenes. In particular, outbreaks of a fatal disease known as alimentary toxic aleukia, which has occurred in Russia since the nineteenth century, have been associated with consumption of over-wintered grains contaminated with *Fusarium* species that produce the trichothecene T-2 toxin. In Japan, outbreaks of a similar disease called akakabi-byo or red mold disease have been associated with grain infected with *Fusarium* species that produce the trichothecene, deoxynivalenol (hereinafter "DON"). Trichothecenes were detected in the toxic grain samples responsible for recent human disease outbreaks in India and Japan. There exists, therefore, a need for agricultural methods for preventing and, crops having reduced levels of, mycotoxin contamination.

Further, trichothecene-producing *Fusarium* species are destructive pathogens and attack a wide range of plant species. The acute phytotoxicity of trichothecenes and their occurrence in plant tissues also suggest that these mycotoxins play a role in the pathogenesis of *Fusarium* on plants. This implies that mycotoxins play a role in disease and, therefore, reducing their toxicity to the plant may also prevent or reduce disease in the plant. Further, reduction in disease levels may have the additional benefit of reducing mycotoxin contamination on the plant and particularly in grain where the plant is a cereal plant.

Various methods of controlling diseases in plants, such as corn ear rot, stock rot or wheat head blight, have been used with varying degrees of success. One method of controlling plant disease has been to apply an antimicrobial chemical to crops. This method has numerous, art-recognized problems. Alternatively, a more recent method involves the use of biological control organisms ("biocontrol") which are natural competitors or inhibitors of the pest organism. However, it is difficult to apply biocontrol to large areas, and even more difficult to cause those living organisms to remain in the treated area for an extended period of time. More recently, techniques in recombinant DNA have provided the opportunity to insert into plant cells cloned genes, which express antimicrobial compounds. However, this technology has given rise to concerns about eventual microbial resistance to well-known, naturally occurring antimicrobials. Thus, a continuing need exists to identify naturally occurring antimicrobial agents, such as proteins, which can be formed by plant cells directly by translation of a single gene.

A trichothecene 3-O-acetyltransferase that catalyzes the acetylation of a number of different *Fusarium* trichothecenes including DON at the C3 hydroxyl group has been identified in *Fusarium sporotrichioides*. (S. P. McCormick, N. J. Alexander, S. C. Trapp, and T. M. Hohn. Disruption of TRI101, the gene encoding trichothecene 3-O-acetyltransferase, from *Fusarium sporotrichioides*. Applied. Environ. Microbiol. 65 (12):5252–5256, 1999.) Acetylation of trichothecenes at the C3-OH significantly reduces their toxicity in vertebrates and plants and results in the reaction product 3-acetyldeoxynivalenol (hereinafter "3ADON") See, Kimura et al. below.

The sequence of structural genes encoding trichothecene 3-O-acetyl transferases from *Fusarium graminearum*, *Fusarium sporotrichioides* as well as sequences of other orthologs has been published. See, e.g. Kimura et al., Biosci. Biotechnol. Biochem., 62 (5) 1033–1036 (1998), and Kimura et al., FEBS Letters, 435, 163–168 (1998). Further, it has been speculated that the gene from *Fusarium sporotrichioides* encoding a trichothecene 3-O-acetyl transferase may be useful in developing plant varieties with increased resistance to *Fusarium*. See., e.g. Hohn, T. M. et al. Molecular Genetics of Host-Specific Toxins in Plant Disease, 17–24 (1998), and Kimura et al. J. Biological Chemistry, 273(3) 1654–1661 (1998).

Prior to the present invention, however, many uncertainties rendered it far from obvious whether expressing trichothecene 3-O-acetyl transferases in a plant would actually lead to trichothecene resistant plants. For example, the reaction catalyzed by the *Fusarium sporotrichioides* trichothecene 3-O-acetyl transferase is reversible and might, therefore have failed to protect plant cells from trichothecenes such as DON. It was also uncertain whether there might be esterases in plant cells that would compete with the 3-O-acetyl transferase activities to generate toxic DON from 3ADON. It was also uncertain how the metabolism of the reaction product 3ADON might affect the plant, e.g. whether introduction of the trichothecene 3-O-acetyltransferase would alter plant growth and development in ways that would negate any positive contribution of the acetyltransferase by for example, interfering with the plant's natural disease resistance mechanisms. It was also uncertain whether 3ADON could be metabolized by the plant to form a novel secondary metabolite with toxic effects. It was also uncertain, even if DON produced by an invading fungus was efficiently converted to 3ADON, whether this conversion would impart enhanced pathogen resistance upon the plant. The above are but a few of the uncertainties in the art before the time of the present invention.

C) DEFINITIONS

Expression refers to the transcription and/or translation of an endogenous gene or a transgene in plants. In the case of antisense constructs, for example, expression may refer to the transcription of the antisense DNA only.

Operably linked/associated when referring to a regulatory DNA sequence being "operably linked to" or "associated with" a DNA sequence that codes for an RNA or a protein refers to the two sequences being situated such that the regulatory DNA sequence affects expression of the coding DNA sequence.

The term "heterologous polynucleotide" or "heterologous DNA" as used herein each refers to a nucleic acid molecule not naturally associated with a host cell into which it is introduced, including genetic constructs, non-naturally occurring multiple copies of a naturally occurring nucleic acid molecule; and an otherwise homologous nucleic acid molecule operatively linked to a non-native nucleic acid molecule. Thus, a heterologous gene in a host cell includes a gene that is endogenous to the particular host cell but has been modified through, for example, the use of DNA shuffling. Thus, the terms encompasses a DNA segment that is foreign or heterologous to the cell, or homologous to the cell but in a position within the host cell nucleic acid in which the element is not ordinarily found.

The terms "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19: 5081 (1991); Ohtsuka et al., *J. Biol. Chem.* 260: 2605–2608 (1985); Rossolini et al., *Mol. Cell. Probes* 8: 91–98 (1994)). The terms "nucleic acid" or "nucleic acid sequence" or "polynucleotide" may also be used interchangeably with gene, cDNA, and mRNA encoded by a gene.

In its broadest sense, the term "substantially similar", when used herein with respect to a nucleic acid molecule, means a nucleic acid molecule corresponding to a reference nucleotide sequence, wherein the corresponding nucleic acid molecule encodes a polypeptide having substantially the same structure and function as the polypeptide encoded by the reference nucleotide sequence, e.g. where only changes in amino acids not affecting the polypeptide function occur. Desirably the substantially similar nucleic acid molecule encodes the polypeptide encoded by the reference nucleotide sequence. The term "substantially similar" is specifically intended to include nucleic acid molecules wherein the sequence has been modified to optimize expression in particular cells, e.g. in plant cells. The percentage of identity between the substantially similar nucleic acid molecule and the reference nucleotide sequence desirably is at least 45%, more desirably at least 65%, more desirably at least 75%, preferably at least 85%, more preferably at least 90%, still more preferably at least 95%, yet still more preferably at least 99%. Preferably, the percentage of identity exists over a region of the sequences that is at least about 50 residues in length, more preferably over a region of at least about 100 residues, and most preferably the sequences are substantially similar over at least about 150 residues. In a most preferred embodiment, the sequences are substantially similar over the entire length of the coding regions. Sequence comparisons may be carried out using a Smith-Waterman sequence alignment algorithm and as described in more detail below (see e.g. Waterman, M. S. Introduction to Computational Biology: Maps, sequences and genomes. Chapman & Hall. London: 1995. ISBN 0-412-99391-0). The local S program, version 1.16, is used with following parameters: match: 1, mismatch penalty: 0.33, open-gap penalty: 2, extended-gap penalty: 2.

Another indication that a nucleic acid sequences is a substantially similar nucleic acid of the invention is that it hybridizes to a nucleic acid molecule of the invention under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes* part I chapter 2 "Overview of principles of hybridization and the strategy of nucleic acid probe assays" Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially similar if the proteins that they encode are substantially similar. This occurs, e.g., when a copy of a nucleic acid is created using the maximum codon degeneracy permitted by the genetic code.

The following are examples of sets of hybridization/wash conditions that may be used to identify homologous nucleotide sequences that are substantially similar to reference nucleotide sequences of the present invention: a test sequence that hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. The polynucleotide of the invention that hybridizes under the above conditions preferably comprises at least 80 base pairs, more preferably at least 50 base pairs and particularly at least 21, and more particularly 18 base pairs. Preferred homologs of use in the invention include nucleic acid molecules that encode an amino acid sequence that is at least 45% identical to SEQ ID NO:2, 6 or 8 as measured, using the parameters described below, wherein the amino acid sequence encoded by the homolog has trichothecene resistance activity, e.g. 3-O-acetyltransferase activity.

The term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is at least 45% identity, more desirably at least 65%, more desirably at least 75%, preferably at least 85%, more preferably at least 90%, still more preferably at least 95%, yet still more preferably at least 99%, using default BLAST analysis parameters and as described in more detail below.

Preferred homologs of the polypeptide of use in the invention comprise those having amino acid sequences that are at least 45% identical to SEQ ID NO:2, 6 or 8, wherein the amino acid sequence encoded by the homolog has trichothecene resistance activity, e.g. 3-O-acetyl transferase activity.

Optimal alignment of nucleic acid or protein sequences for comparison can be conducted as described above and, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403–410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873–5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

A further indication that two nucleic acid sequences or proteins are substantially similar is that the protein encoded by the first nucleic acid is immunologically cross reactive with, or specifically binds to, the protein encoded by the second nucleic acid. Thus, a protein is typically substantially similar to a second protein, for example, where the two proteins differ only by conservative substitutions.

The phrase "specifically (or selectively) binds to an antibody," or "specifically (or selectively) immunoreactive with," when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to the protein with the amino acid sequence encoded by any of the nucleic acid sequences of the invention can be selected to obtain antibodies specifically immunoreactive with that protein and not with other proteins except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) *Antibodies, A Laboratory Manual*, Cold Spring Harbor Publications, New York "Harlow and Lane"), for a description of immunoassay formats and conditions that can be used to determine specific immunoreactivity. Typically a specific or selective reaction will be at least twice background signal or noise and more typically more than 10 to 100 times background.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a protein also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a protein is implicit in each described sequence.

Furthermore, one of skill will recognize that individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton (1984) *Proteins*, W.H. Freeman and Company. In addition, individual substitutions, deletions or additions which alter, add or delete a single amino acid or a small percentage of amino acids in an encoded sequence are also "conservatively modified variations."

A "subsequence" refers to a sequence of nucleic acids or amino acids that comprise a part of a longer sequence of nucleic acids or amino acids (e.g., protein) respectively.

Nucleic acids are "elongated" when additional nucleotides (or other analogous molecules) are incorporated into the nucleic acid. Most commonly, this is performed with a polymerase (e.g., a DNA polymerase), e.g., a polymerase which adds sequences at the 3' terminus of the nucleic acid.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross-over oligonucleotide. For indirect recombination, no more than one of the sequences is an actual substrate for recombination, and in some cases, neither sequence is a substrate for recombination.

A "specific binding affinity" between two molecules, for example, a ligand and a receptor, means a preferential binding of one molecule for another in a mixture of molecules. The binding of the molecules can be considered specific if the binding affinity is about $1 \times 10^4$ $M^{-1}$ to about $1 \times 10^6$ $M^{-1}$ or greater.

Substrate: a substrate is the molecule that an enzyme naturally recognizes and converts to a product in the biochemical pathway in which the enzyme naturally carries out its function, or is a modified version of the molecule, which is also recognized by the enzyme and is converted by the enzyme to a product in an enzymatic reaction similar to the naturally-occurring reaction.

Transformation: a process for introducing heterologous DNA into a cell, tissue, or insect. Transformed cells, tissues, or insects are understood to encompass not only the end product of a transformation process, but also transgenic progeny thereof.

"Transformed," "transgenic," and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

D) SUMMARY

It is an object of the invention to provide a plant cell or cells comprising a heterologous polynucleotide encoding a gene product that is expressed in the plant cell wherein the gene product comprises trichothecene resistance activity.

Another object of the invention is to provide a plant comprising the above described plant cell wherein the plant is resistant to a trichothecene.

Another object of the invention is to provide a plant that is resistant to a trichothecene where the trichothecene comprises a C-3 hydroxyl group.

Another object of the invention is to provide a plant wherein the gene product is a 3-O-acetyltransferase.

Another object of the invention is to provide a plant of the invention wherein the heterologous polynucleotide is substantially similar to the nucleic acid sequence of SEQ ID NOs:1, 5 or 7.

Another object of the invention is to provide a plant of the invention wherein the heterologous polynucleotide comprises the nucleic acid sequence of SEQ ID NO:1, 5 or 7 or homologs thereof.

Another object of the invention is to provide a plant wherein the gene product is a polypeptide comprising a sequence substantially similar to SEQ ID NO:2, 6 or 8.

Another object of the invention is to provide a plant wherein the heterologous polynucleotide comprises the nucleic acid sequence of SEQ ID NO:1, 5 or 7.

Another object of the invention is to provide a plant comprising a heterologous polynucleotide, which comprises a consecutive 18 base pair portion identical in sequence to a consecutive 18 base pair portion set forth in SEQ ID NO:1, 5 or 7.

Another object of the invention is to provide a plant resistant to a trichothecene selected from the group consisting T-2 toxin, HT-2 toxin, isotrichodermol, 4,15-diacetoxyscirpenol (hereinafter "DAS"), 3-deacetylcalonectrin, 3,15-dideacetylcalonectrin, scirpentriol, neosolaniol; type B: 15-acetyldeoxynivalenol, nivalenol, 4-acetylnivalenol (fusarenone-X), 4,15-diacetylnivalenol, 4,7,15-acetylnivalenol, and DON.

Another object of the invention is to provide a plant resistant to DAS or DON.

Another object of the invention is to provide a seed of any of the plants of the invention.

Another object of the invention is to provide anyone of the above-described plants wherein the plant is a wheat, maize, barley or rice plant.

Another object of the invention is to provide a plant that is resistant to a fungus that produces a trichothecene comprising a C-3 hydroxyl group.

Another object of the invention is to provide a plant that is resistant to *Fusarium*, *Trichothecium* or *Myrothecium*.

Another object of the invention is to provide a plant that is resistant to *Fusarium*, in particular but not limited to *Fusarium graminearum*, *Fusarium culmorum*, *Fusarium sporotrichioides*, *Fusarium poae*, *Fusarium sambucinum*, *Fusarium equiseti*, *Fusarium acuminatum*, *Fusarium lateritium*, and *Fusarium pseudograminearum*.

Another object of the invention is to provide a plant that is resistant to *Fusarium graminearum*.

Another object of the invention is to provide a plant of the invention as described above wherein the heterologous polynucleotide is a microbial polynucleotide.

Another object of the invention is to provide a plant of the invention as described above wherein the microbial polynucleotide is a yeast or fungal polynucleotide.

Another object of the invention is to provide a plant of the invention as described above wherein the fungal polynucleotide is a *Fusarium* polynucleotide.

Another object of the invention is to provide a plant of the invention as described above wherein the *Fusarium* polynucleotide is a *Fusarium graminearum* or *Fusarium sporotrichioides* polynucleotide.

Another object of the invention is to provide a plant as described above wherein the plant is resistant to a fungus that produces a trichothecene.

Another object of the invention is to provide a plant as described above wherein the plant is resistant to a fungus that produces a trichothecene comprising a C-3 hydroxyl group.

Another object of the invention is to provide a method for producing a trichothecene resistant plant comprising the steps of:
  a) transforming a plant cell with a heterologous gene encoding a gene product, wherein the gene product increases resistance to a trichothecene; and
  b) expressing the gene product at a biologically significant level.
  c) regenerating the plant cell into a plant; and
  d) selecting a plant having increased resistance to a trichothecene.

Another object of the invention is to provide a method as described above further comprising the step of selecting a plant on which there is reduced growth of a fungus where the fungus produces a trichothecene.

Another object of the invention is to provide a method as described above wherein the fungus is of the genera *Fusarium*.

Another object of the invention is to provide a trichothecene resistant plant obtained according to the above-described methods.

Another object of the invention is to provide a seed produced by selling or outcrossing a plant of the invention as described above, wherein a plant grown from the seed has an increased resistance to trichothecene.

Another object of the invention is to provide a method of preventing mycotoxin crop contamination comprising growing a plant of the invention as described above, wherein the plant is a crop plant.

Another object of the invention is to provide a method of preventing fungal growth on a crop, comprising growing a plant of the invention as described above, wherein the plant is a crop plant.

Another object of the invention is to provide a method of selecting transformed host cells, the method comprising: transforming a host cell with a nucleic acid construct encoding a trichothecene 3-O-acetyltransferase, and growing the transformed host cell in the presence of a trichothecene selective agent.

Another object of the invention is to provide a method of selecting transformed host cells wherein the host cells are plant cells, or microbial cells, particularly where the microbial cells are fungal cells.

Another object of the invention is to provide a method of selecting transformed host cells as described above where the host cell is further transformed with a second polynucleotide of interest.

Another object of the invention is to provide a method of selecting transformed host cells wherein in the trichothecene is selected from the group the group consisting T-2 toxin, HT-2 toxin, isotrichodermol, DAS, 3-deacetylcalonectrin, 3,15-dideacetylcalonectrin, scirpentriol, neosolaniol; type B: 15-acetyldeoxynivalenol, nivalenol, 4-acetylnivalenol (fusarenone-X), 4,15-diacetylnivalenol, 4,7,15-acetylnivalenol, and DON.

E) DETAILED DESCRIPTION

Description of the Sequences:

| | |
|---|---|
| SEQ ID NO:1 | is a cDNA sequence from *Fusarium sporotrichioides* encoding a polypeptide of the invention having trichothecene resistance activity. |
| SEQ ID NO:2 | is the polypeptide having trichothecene resistance activity encoded by SEQ ID NO:1. |
| SEQ ID NO:3 | is a DNA primer. |
| SEQ ID NO 4: | is a DNA primer. |
| SEQ ID NO:5 | is a DNA sequence from *Fusarium graminearum* encoding a polypeptide of the invention having trichothecene resistance activity. |
| SEQ ID NO:6 | is the polypeptide having trichothecene resistance activity encoded by SEQ ID NO:5. |
| SEQ ID NO.7 | is a DNA sequence from *Saccharomyces cerevisiae* encoding a polypeptide of the invention having trichothecene resistance activity. |
| SEQ ID NO.8 | is the polypeptide having trichothecene resistance activity encoded by SEQ ID NO:7. |
| SEQ ID NO.9 | is the DNA sequence of pCIB9818. |
| SEQ ID NO.10 | is the DNA sequence of pAgroTRIr. |
| SEQ ID NO.11 | is the DNA sequence of pNOV1704. |

DESCRIPTION OF THE DRAWING

FIG. 1 depicts positions C-3 and C-8 on the representative trichothecene Deoxynivalenol.

The present invention relates to transgenic hosts particularly, transgenic plants, plant tissues, plant seeds, and plant cells comprising a heterologous polynucleotide encoding a gene product where the gene product comprises trichothecene resistance activity and methods of making and using the same. Trichothecene resistance activity as used herein refers to an activity that reduces or inhibits the phytotoxicity of a trichothecene, particularly to a fungus and/or plant, in a particular embodiment of the invention trichothecene resistance activity refers to an activity that transfers an acetate to the C-3 position (see FIG. 1) of a trichothecene.

The present invention further relates to transgenic hosts, particularly, transgenic plants, plant tissues, plant seeds, and plant cells expressing a heterologous polynucleotide encoding a gene product, the gene product having trichothecene resistance activity, particularly an acetyl transferase gene product, more particularly a 3-O-acetyl transferase gene product, more particularly trichothecene 3-O-acetyl transferase gene product and methods of making and using the same. Expression of the heterologous polynucleotide of the invention comprises the synthesis of RNA and may be detected by northern blot analysis. Particularly, expression of the heterologous polynucleotide of the invention may detected where a labeled probe derived from a heterologous nucleotide of the invention, in particular embodiments, from SEQ ID NOs. 1, 5 or 7, hybridizes with RNA isolated from a transgenic plant of the invention in 7% sodium dodecyl sulfate (SDS), 0.5 M Sodium phosphate pH 7.0, 1 mM EDTA, 10 mg/ml BSA at 65° C. with washing in 0.5% BSA (fraction V), 5% SDS, 40 mM Sodium phosphate pH 7.0, 1 mM EDTA, 0.25 M sodium chloride at 65° C., preferably in 1% SDS, 40 mM Sodium phosphate pH 7.0, 1 mM EDTA, 0.125 M sodium chloride at 65° C., and preferably in 1% SDS, 40 mM Sodium phosphate pH 7.0, 1 mM EDTA at 65° C.

The present invention further relates to transgenic plants plant tissues, plant seeds, and plant cells, expressing a heterologous polynucleotide of the invention where the plant, plant cell, plant tissue or plant seed is trichothecene resistant. Trichothecene resistant plants, plant cells, plant tissues and plant seeds as used herein are those which are capable of metabolism in the presence of a trichothecene which may be determined as described in Example 7 below. In a particular embodiment, trichothecene resistant plants, plant tissues, plant cells and plant seeds which have a specific enzyme activity of at least 10 nmol triacetoxyscirpenol (hereinafter "TAS")/microgram protein/15 min incubation at saturating substrate levels, more particularly at least 5 nmol TAS/microgram protein/15 min, more particularly at least 1 nmol TAS/microgram protein/15 min, more particularly at least 0.8 nmol TAS/microgram protein/15 min more particularly at least 0.5 nmol TAS/microgram protein/ 15 min, more particularly a specific activity of 0.25 mmol TAS/microgram protein/15 minute, more particularly a specific activity of 0.1 nmol TAS/microgram protein/15 min., more particularly a specific activity of 0.05 nmol TAS/microgram protein/15 min and even more particularly a specific activity of 0.01 nmol TAS/microgram protein/15 min above background levels of activity that occur naturally in a wild type control, particularly as determined in an assay as described in Example 6 below.

Trichothecene resistant plants of the invention comprise those of which a greater percentage of the seed germinate and form roots in the presence of a trichothecene than the seed from a wild type control where the trichothecene is present at a concentration of at least 5 microgram/ml, more preferably at least 10 microgram/ml, more at least preferably 15 microgram/ml, more preferably at least 20 microgram/ml and more preferably at least 25 microgram/ml. In a particularly preferred embodiment, trichothecene resistant plants of the invention comprise those of which at least 10% more seed, more preferably at least 20%, more preferably at least 30%, more preferably at least 40%, more preferably at least 50%, more preferably at least 60% more seed, more preferably at least 70% more seed, more preferably at least 80% more seed and more preferably at least 90% more seed germinate and form roots in the presence of a trichothecene than the seed of a wild type control.

Trichothecenes are frequently divided into several different structural groups. A particular embodiment of the present invention is drawn to resistance to group A and B trichothecenes. Groups A and B comprise the *Fusarium* trichothecenes and are differentiated primarily by the absence (group A) or presence (group B) of a carbonyl functional group at position C-8. FIG. 1 depicts the group B trichothecene, DON that, accordingly, comprises a carbonyl group at the C-8 position.

The present invention is more particularly drawn to resistance to trichothecenes, which contain a C-3 hydroxyl. FIG. 1 depicts position C-3 on the representative trichothecene DON. Such trichothecenes include T-2 toxin, HT-2 toxin, isotrichodermol, DAS, 3-deacetylcalonectrin, 3,15-dideacetylcalonectrin, scirpentriol, neosolaniol; 15-acetyldeoxynivalenol, nivalenol, 4-acetylnivalenol (fusarenone-X), 4,15-diacetylnivalenol, 4,7,15-acetylnivalenol, and DON and their various acetylated derivatives.

In a particular embodiment, the trichothecene resistant plant, cell, tissue or seed thereof is resistant to a trichothecene producing fungus, particularly a fungus of the genera *Fusarium*. Fungus resistance as used herein refers to no initiation of infection after fungal inoculation or reduced spread of the infection after fungal inoculation compared to a wild type control.

In a preferred embodiment, a fungal resistant transgenic plant of the present invention is a cereal plant and under fungal challenge comprises less infected kernels or seeds compared to a wild type control, preferably at least a 10% decrease of infected kernels or seeds compared to the same number of kernels or seeds evaluated in a wild type control, more preferably at least a 20% decrease, more preferably at least a 40% decrease and more preferably at least a 50% decrease of infected kernels compared to the same number of kernels or seeds in a wild type control. The fungal resistant transgenic cereal plants of the invention comprise but are not limited to maize, wheat, barley, rice, and oats.

In wheat, fungal spread in the head may be evaluated as described in Example 9 below, by counting the number of symptomatic and asymptomatic spikelets on each inoculated head and calculating the percentage of spikelets on each head that are symptomatic. In a preferred embodiment, fungal resistant wheat of the present invention comprises, under fungal challenge, less infected spikelets than the wild type control, preferably at least a 10% decrease of infected spikelets compared to the same number of spikelets evaluated in a wild type control, more preferably at least a 20% decrease, more preferably at least a 40% decrease and more preferably at least a 50% decrease of infected spikelets compared to the same number of spikelets in a wild type control.

In maize, fungal spread in the ear may be evaluated by visual estimation of the percentage of infected kernels as described further in Example 9 below. In a preferred embodiment, fungal resistant maize of the invention, under fungal challenge, comprise less infected kernels than the wild type control, preferably at least a 10% decrease in infected kernels compared to the number of infected kernels in the same number of ears visibly estimated in a wild type control, more preferably at least a 20% decrease, more preferably at least 30% decrease, more preferably at least a 40% decrease and more preferably at least a 50% decrease in infected kernels compared to the same number of ears visibly estimated in a wild type control. In maize, internal fungal spread in the stalk may be visually evaluated by splitting open the stalk and assessing the amount of discoloration. In a preferred embodiment of the invention, the transgenic maize of the invention comprises less internal and/or external discoloration of the stalk compared to a wild type control.

In another, preferred embodiment fungal resistant plants of the invention comprise those of which a greater percentage of seed germinate in the presence of fungal challenge than germinate in the wild type control. In a particularly preferred embodiment, fungal resistant plants of the invention comprise those of which at least 10% more seed, more preferably at least 20%, more preferably at least 30%, more preferably at least 40%, more preferably at least 50%, more preferably at least 60% more seed, more preferably at least 70% more seed, more preferably at least 80% more seed and more preferably at least 90% more seed, more preferably at least 100% more seed, more preferably at least 150% more seed germinates in the presence of *Fusarium* than does seed from the wild type control.

In another preferred embodiment, fungal resistant transgenic plants producing seed or kernels having less mycotoxin, e.g. trichothecene contamination, than the seed of a wild type control are provided. In a particularly preferred embodiment crop plants and more particularly cereal plants producing seed having at least 10% less trichothecene, more preferable at least 20% less trichothecene, more preferably at least 30% less trichothecene, more preferably at least 40% less trichothecene, more preferably at least 50% less trichothecene, more preferably at least 60% less trichothecene, more preferably at least 70% less trichothecene and more preferably at least 80% less trichothecene contamination than a wild type control are provided. Trichothecene contamination may be determined as described in Example 10 below.

The polynucleotides of use in the invention include heterologous polynucleotides encoding acetyl transferases, particularly those encoding acetyl transferases capable of conferring trichothecene resistance, more particularly those encoding trichothecene 3-O-acetyltransferases. In a particular embodiment, the heterologous polynucleotide of the invention may be derived from but is not limited to fungal origin, more particularly from *Fusarium, Trichothecium*, and *Myrothecium* origin, more particularly from a *Fusarium* species such as *F. acuminatum, F. crookwellense, F. culmorum, F. equiseti, F. graminearum* (*Gibberella zeae*)*, F. lateritium, F. poae, F. sambucinum* (*G. pulicaris*), and *F. sporotrichioides*. Heterologous polynucleotides of use in the invention include SEQ ID NO:1, 5 and/or 7 and sequences substantially similar to SEQ ID NO:1, 5 and/or 7.

A polynucleotide of use in the invention can be incorporated into host cells, such as plant, fungal or bacterial cells, using conventional recombinant DNA technology. Generally, this involves inserting the polynucleotide into an expression system to which the polynucleotide is heterologous using standard cloning procedures known in the art. The vector contains the necessary elements for the transcription and translation of the polynucleotide of use in the invention in a host cell containing the vector. A large number of vector systems known in the art can be used, such as plasmids, bacteriophage viruses and other modified viruses. The components of the expression system may also be modified to increase expression. For example, truncated sequences, nucleotide substitutions, nucleotide optimization or other modifications may be employed. Expression systems known in the art can be used to transform virtually any crop plant cell under suitable conditions. A heterologous polynucleotide of the inventions is preferably stabley transformed and integrated into the genome of the host cells. In another preferred embodiment, the heterologous polynucleotide of the inventions is located on a self-replicating vector. Examples of self-replicating vectors are viruses, in particular Gemini viruses. Transformed cells can be regenerated into whole plants such that the chosen form of the polynucleotide of the invention confers trichothecene resistance in the transgenic plants.

I. Requirements for Construction of Plant Expression Cassettes

A polynucleotide of the invention intended for expression in transgenic plants is first assembled in an expression cassette behind a suitable promoter expressible in plants. The expression cassettes may also comprise any further sequences required or selected for the expression of the heterologous polynucleotide of the invention. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described infra. The following is a description of various components of typical expression cassettes.

1. Promoters

The selection of the promoter used in expression cassettes will determine the spatial and temporal expression pattern of the heterologous polynucleotide of the invention in the transformed plant. Selected promoters will express heterologous polynucleotides of the invention in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters known in the art can be used. For example, for constitutive expression, the CaMV 35S promoter, the rice actin promoter, or the ubiquitin promoter may be used. For regulatable expression, the chemically inducible PR-1 promoter from tobacco or *Arabidopsis* may be used (see, e.g., U.S. Pat. No. 5,689,044).

2. Transcriptional Terminators

A variety of transcriptional terminators are available for use in expression cassettes. These are responsible for the termination of transcription beyond the heterologous polynucleotide of the invention and its correct polyadenylation. Appropriate transcriptional terminators are those that are known to function in plants and include the CaMV 35 S terminator, the tml terminator, the nopaline synthase terminator and the pea rbcS E9 terminator. These can be used in both monocotyledonous and dicotyledonous plants.

3. Sequences for the Enhancement or Regulation of Expression

Numerous sequences have been found to enhance gene expression from within the transcriptional unit and these sequences can be used in conjunction with the polynucleotides of this invention to increase their expression in transgenic plants. For example, various intron sequences such as introns of the maize AdhI gene have been shown to enhance expression, particularly in monocotyledonous cells. In addition, a number of non-translated leader sequences derived from viruses are also known to enhance expression, and these are particularly effective in dicotyledonous cells.

4. Coding Sequence Optimization

The coding sequence of the selected gene optionally is genetically engineered by altering the coding sequence for optimal expression in the crop species of interest. Methods for modifying coding sequences to achieve optimal expression in a particular crop species are well known (see, e.g. Perlak et al., *Proc. Natl. Acad. Sci. USA* 88: 3324 (1991); and Koziel et al., *Bio/technol.* 11: 194 (1993); Fennoy and Bailey-Serres. *Nucl. Acids Res.* 21: 5294–5300 (1993). Methods for modifying coding sequences by taking into account codon usage in plant genes and in higher plants, green algae, and cyanobacteria are well known (see table 4 in: Murray et al. *Nucl. Acids Res.* 17: 477–498 (1989); Campbell and Gowri *Plant Physiol.* 92: 1–11(1990).

5. Targeting of the Gene Product within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104–15109 (1988)). Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous products encoded by DNA sequences to these organelles. In addition, sequences have been characterized which cause the targeting of products encoded by DNA sequences to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al. Plant Molec. Biol. 14: 357–368 (1990)). By the fusion of the appropriate targeting sequences described above to a heterologous polynucleotide of the invention, it is possible to direct a resulting product to any organelle or cell compartment.

B. Construction of Plant Transformation Vectors

Numerous transformation vectors available for plant transformation are known to those of ordinary skill in the plant transformation arts, and the polynucleotides pertinent to this invention can be used in conjunction with any such vectors. The selection of vector will depend upon the preferred transformation technique and the target species for transformation. For certain target species, different selection markers may be preferred. Selection markers used routinely in transformation include the nptII gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methotrexate (Bourouis et al., EMBO J. 2(7): 1099–1104 (1983)), and the EPSPS gene, which confers resistance to glyphosate (U.S. Pat. Nos. 4,940,935 and 5,188,642), phosphomannose isomerase gene, manA, which confers a selective metabolic advantage in the presence of mannose (U.S. Pat. No. 5,767,378 which is incorporated herein by reference in its entirety and Miles & Guest, GENE, 32:41–48 (1984)). PAT selectable marker that confers resistance to BASTA (Sung H. Park et al., In Vitro Cell. Dev. Biol.-Plant, 34: 117–121 (1998)).

1. Vectors Suitable for *Agrobacterium* Transformation

Many vectors are available for transformation using *Agrobacterium tumefaciens*. These typically carry at least one T-DNA border sequence and include vectors such as pBIN19 (Bevan, Nucl. Acids Res. (1984)). Typical vectors suitable for *Agrobacterium* transformation include the binary vectors pCIB200 and pCIB2001, as well as the binary vector pCIB10 and hygromycin selection derivatives thereof. (See, for example, U.S. Pat. No. 5,639,949).

2. Vectors Suitable for non-*Agrobacterium* Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. Typical vectors suitable for non-*Agrobacte*-

*rium* transformation include pCIB3064, pSOG19, and pSOG35. (See, for example, U.S. Pat. No. 5,639,949).

C. Transformation Techniques

Once the polynucleotide of interest has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, micro-injection, and microprojectiles. In addition, bacteria from the genus *Agrobacterium* can be utilized to transform plant cells.

Transformation techniques for dicotyledons are well known in the art and include *Agrobacterium*-based techniques and techniques that do not require Agrobacterium. Non-*Agrobacterium* techniques involve the uptake of exogenous genetic material directly by protoplasts or cells. This can be accomplished by PEG or electroporation mediated uptake, particle bombardment-mediated delivery, or micro-injection. In each case the transformed cells are regenerated to whole plants using standard techniques known in the art.

Transformation of most monocotyledon species has now also become routine. Preferred techniques include direct gene transfer into protoplasts using PEG or electroporation techniques, particle bombardment into callus tissue, as well as *Agrobacterium*-mediated transformation. Target tissue may be derived from such sources as wheat cultivar UC703 or maize genotype CG000526. For example, *Agrobacterium* mediated transformation of maize may be carried out as described in U.S. Pat. No. 6,162,965, which is herein incorporated by reference in its entirety which correspondingly published as WO 98/54961, and of barley may be carried out as described by: M. Cho, J. Wong, C. Marx, W. Jiang, P. Lemaux and B. Buchanan (1999). Overexpression of thioredoxin h leads to enhanced activity of starch debranching enzyme (pullulanase) in barley grain. PNAS 96: 14641–14646; S. Zhang, M. Cho, T. Koprek, R. Yun, P. Bregitzer and P. Lemaux (1999). Genetic transformation of commercial cultivars of oat (*Avena sativa* L.) and barley (*Hordeum vulgare* L.) using in vitro shoot meristematic cultures derived from germinated seedlings. Plant Cell Rep. 18: 959–966; P. Bregitzer, S. Harlbert and P. Lemaux (1998). Somaclonal variation in the progeny of transgenic barley. TAG 96: 421–425; M. Cho, W. Jiang and p. Lemaux (1998). Transformation of recalcitrant barley cultivars through improvement of regenerability and decreased albinism. Plant sci. 138: 229–244; P. Lemaux, m. Cho, S. Zhang, and p. Bregitzer (1998). Transgenic cereals: *Hordeum vulgare* L.—current status and future prospects. In: Vasil I, Phillips R (eds) Molecular Improvement of Cereal Crops, Kluwer Academic Publ, Dordrecht, The Netherlands, pp 255–316; S. Zhang, R. Williams-Carrier, D. Jackson, and P. Lemaux (1998). Expression of CDC2Zm and KNOTTED1 during in vitro auxillary shoot meristem proliferation and adventitious shoot meristem formation in maize (*Zea mays* L.) and barley (*Hordeum vulgare* L.). Planta 204: 542–549; D. McElroy, J. Louwerse, S. McElroy and P. Lemaux (1997). Development of a simple transient assay for Ac/Ds activity in cells of intact barley tissue. Plant J. 11: 157–165; S. Tingay, D. McElroy, R. Kalla, S. Fieg, M. Wang, S. Thornton and R. Brettell (1997). *Agrobacterium tumefaciens*-mediated bareley transformation. The Plant J. 11: 1369–1376; J. Qureshi, Z. Basri, R. Singh, R. Burton, M. Dalton, J. Kollmorgen and G. Fincher. 1988. *Agrobacterium*-mediated transformation of two varieties of barley (*Hordeum vulgare* L.) Proc. $42^{nd}$. Conference of Australian Society for Biochemistry and Molecular Biology, Sep. 28–Oct. 1, 1998, Adelaide, Australia; J. Qureshi, R. Singh, Z. Basri, R. Stewart, R. Burton, J. kollmorgen and G. Fincher (1997). Strategies for genetic transformation of elite Australian barley varieties. Proc. 8th. Aust. Barley Technical symp. Gold Coast, Queensland, 7–12 Sep. 1997. 2:8.9–11; P. Lemaux, M. Cho, J. Louwerse, R. Williams and Y. Wan (1996). Bombardment-mediated transformation methods for barley. Bio-Rad US/EG Bull 2007: 1–6; T. Koprek, R. Hansch, A. Nerlich, R. Mendel and J. Schulze (1996). Fertile transgenic barley of different cultivars obtained by adjustment of bombardment conditions to tissue response. Plant Sci. 119: 79–91; T. Hagio, T. hirabayashi, H. Machii and H. Tomutsune (1995). Production of fertile transgenic barley (*Hordeum vulgare* L.) plants using the hygromycin-resistance marker. Plant Cell Rep. 14: 329–334; H. Funatsuki, H. Kuroda, M. Kihara, P. Lazzeri, E. Muller, H. Lorz and I. Kishinami (1995). Fertile transgenic barley regenerated by direct DNA transfer to protoplasts. TAG 91: 707–712; A. Jahne, D. Becker, R. Brettschneider and H. Lorz (1994). Regeneration of transgenic, microscpore-derived, fertile barey. TAG 89: 525–533; Y. Wan and P. Lemaux (1994). Generation of large numbers of independently transformed fertile barley plants. Plant Physiol. 104: 37–48.

II. Breeding

The polynucleotides of the invention can be utilized to confer trichothecene resistance to a wide variety of plant cells, including those of gymnosperms, monocots, and dicots. Although the heterologous polynucletide of the invention can be inserted, e.g. transformed into any plant cell falling within these broad classes, it is particularly useful in crop plant cells, such as rice, wheat, barley, rye, corn, oats, potato, sweet potato, turnip, squash, pumpkin, zucchini, melon, soybean, and sorghum. The polynucleotides of use in the invention rendering a plant trichothecene resistant may be used in combination with other characteristics important for production and quality. The polynucleotides of the invention can be incorporated into plant lines through breeding approaches and techniques known in the art.

Where a trichothecene resistant gene allele is obtained by transformation into a crop plant or plant cell culture from which a crop plant can be regenerated, it is moved into commercial varieties using traditional breeding techniques to develop a trichothecene resistant crop without the need for genetically engineering the allele and transforming it into the plant.

III. Selection System

In another embodiment, the heterologous polynucleotide of use in the invention, can also be used as a selectable marker in transformation procedures. In this aspect the host cell is transformed with a second heterologous polynucleotide of interest as well as a heterologous polynucleotide of the invention which encodes a gene product comprising trichothecene resistance activity, using expressions cassettes and transformation techniques exemplified above and known in the art. After transformation, the transformed cells are selected for their ability to survive when exposed to a trichothecene, particularly DAS or DON or T-2 toxin. The host cell may be a eukaryotic or prokaryotic host cell using transformation and expression systems known in the art. The host cell may be a plant cell, a fungal cell, a bacterial cell, a yeast cell, an animal cell, or an insect cell.

In a particularly preferred embodiment of the invention, a polynucleotide which encodes a gene product comprising trichothecene resistance activity is used as a selectable marker in plant cell transformation methods. For example, plants, plant tissue, plant seeds, or plant cells expressing at least a second heterologous DNA sequence of interest can also be transformed to express a sequence encoding a polypeptide comprising a sequence substantially similar to that of SEQ ID NO:2, 6 or 8. The transformed cells are transferred to medium containing a phytotoxic trichothecene, particularly DAS and/or DON and/or T-2 toxin, in an amount sufficient to inhibit the growth or survivability of plant cells not expressing the polypeptide substantially similar to that having the amino acid sequence of SEQ ID NO:2, 6 or 8, wherein only the transformed cells will grow or will be unstunted. Concentrations of trichothecenes useful for selection of plants expressing the polypeptide substantially similar to that having the amino acid sequence of SEQ ID NO:2, 6 or 8 range from 1 ug/ml to 90 ug/ml. The method is applicable to any plant cell capable of expressing a polynucleotide comprising a nucleotide sequence substantially similar to that of SEQ ID NO: 1, 5 or 7, and can be used with any heterologous DNA sequence of interest. Expression of the second heterologous DNA sequence and the heterologus polynucleotide of the of the invention can be driven by the same promoter functional in plant cells, or by separate promoters.

F) EXAMPLES

The following examples further describe the materials and methods used in carrying out the invention and the subsequent results. They are offered by way of illustration, and their recitation should not be considered as a limitation of the claimed invention.

Example 1

Composition of pNOV1700, pCIB9818, pAgroTRIr and pNov 1704

1. pNOV1700:

pNOV1700 was deposited under the terms of the Budapest Treaty on Mar. 19, 1999, with the Agricultural Research Service, Patent Culture Collection (NRRL), Northern Regional Research Center, 1815 Northern University Street, Peoria, Ill. 61604, USA and assigned accession number NRRL B-30117.

Accordingly, pNOV1700 comprises SEQ ID NO. 1 operably linked to the *Z.mays* ubiquitin promoter, including a portion of the exon and intron, and to the nopaline synthase polyadenylation signal.

2. pCIB9818

Plasmid pCIB9818 is a 6111 base pair circular plasmid having a DNA sequence according to SEQ ID NO. 9. The *Z. mays* ubiquitin promoter, base 12 to 1993 of SEQ ID NO.9, including a portion of the exon, base 896 to 1011, and the intron, base 1047 to 1993, is operably linked to the phosphate mannose isomorase selectable marker, base pair 2090 to 3193, the inverted PEPC intron #9 from base 3248 to 3355 and the termination sequence of the CaMV 35S gene, base 3357 to 3434.

3. pAgroTRIr

Plasmid pAgroTRIr is a 13,737 base pair circular binary vector having a DNA sequence according to SEQ ID NO. 10. Accordingly, pAgroTRIr comprises a selectable marker operable linked to a promoter and termination sequence and the polynucleotide region of SEQ ID NO:1 behind and in frame with the *Arabidopsis thalliana* UBI 3 promoter (S. Norris, S. Meyer, and J. Callus, Plant Molecular Biology 22:895–906, (1993)) and in front of and in frame with the nos polyadenylation signal.

4. pNov 1704

Plasmid pNOV1704 is a 12949 base pair circular binary vector having a DNA sequence according to SEQ ID NO. 11. The *Z. mays* ubiquitin promoter, base 11 to 1992 of SEQ ID NO.11(including exon 1 895 to 1010 and intron 1 1046 to 1992), is operably linked to the phosphate mannose isomorase selectable marker sequence, base 2089 to 3192, and the nopaline synthase termination sequence, base 3557 to 3688. pNOV1704, further comprises the *Z. mays* ubiquitin promoter, base 9218 to 11218 (including exon 1 10,110 to 10224 and intron 1 10225 to 11218) operably linked to the trichothecene 3-O-acetyl transferase sequence of SEQ ID NO.1, at base 11,234 to 12,662 and the nos termination sequence 12667 to 12935.

Example 2

Wheat Transformation, Selection and Regeneration

Transformation

Immature zygotic embryos (0.75–1.25 mm) are dissected from surface sterilized wheat caryopses (10% Chlorox X 10 minutes) then plated scutellum up onto an MS based medium (Murashige and Skoog, (1962) Physiol. Plant 15:473–439) supplemented with 3% sucrose, 3 mg/liter 2,4-D (dichlororpheoxyacetic acid), 150 mg/l glutamine, 75 mg/l asparagine and solidified with 0.7% phytagar (3MS3S medium). The embryos are incubated in the dark at 28° C. for 5–10 days prior to bombardment. The optimal time for bombardment is 6–7 days post-plating. Four hours prior to bombardment, the embryos are placed on a plasmolysis medium (same medium described above but with 15% maltose added in place of the sucrose) and arranged in a 2.5 cm diameter circle with scutellum facing up.

pNOV1700, described in Example 1 above, is digested with PvuII and XmnI and a 4117 bp fragment comprising a polynucleotide region having a sequence according to SEQ ID NO:1 as well as the ubiquitin promoter and NOS polyadenylation signal is isolated. pCIB9818, also described in Example 1 above, is digested with AscI and the 4246 bp fragment comprising the UBI maize promoter, selectable marker and CaMV 35S termination sequence is isolated.

The isolated DNA fragments are precipitated onto 0.3 micro meter gold particles using the standard Sanford method. While continuously vortexing, 5 microgram of the isolated fragment DNA per construct, 50 ul of 2.5 M $CaCl_2$ and 20 ul of 0.1 M spermidine are added to an eppendorf tube that contains 50 ul of 50% glycerol and 3 mg gold. The DNA/gold mixture is given two ethanol washes. After discarding the supernatant from the last wash, ethanol is added to make a final volume of 70 ul. This provides six shots per tube of gold/DNA. The target plates are shot twice so that gives a delivery of approximately 3 microgram DNA (if 5 microgram each of 2 constructs is used which is usually the case) and 1.0 mg gold per target plate. The rupture pressure used is 1100 psi. After bombardment, the target plates are returned to the dark overnight. After approximately 24 hours of plasmolysis, the embryos are removed to 3MS3S and returned to the dark for 3 weeks of callus initiation. No subculturing is done during this time.

Selection/Regeneration

The embryogenic tissue that develops during the 3-week initiation period is dissected away from non-embryogenic tissue and placed on a regeneration/selection medium. The basic regeneration medium is 3MS3S without the 2,4-D but with 1 mg/1 GA3 (Gibberellin $A_3$) NAA (1-Naphtheleneacetic Acid) and NAA added instead (called NG medium). 10 g/l mannose and 5 g/l sucrose is added (NG1M.5S). The tissue is subjected to this initial phase of regeneration and selection for 2 weeks. For most of the 2 week period the tissue is in the light room. Shoot and root development begins during this phase and after 2 weeks all tissue is taken to the next stage.

For the second phase of regeneration and selection with mannose selection, mannose is decreased to 5 g/l and the sucrose increased to 20 g/l (MS2S.5M). The tissue normally stays on these media for approximately 4 weeks time during which further shoot and root development occurs.

Vigorously growing plantlets with good color, and root and shoot development are removed from plates and placed in larger containers called GA7's. This is the final stage of selection and regeneration The medium contains only 1/2MS salts and 15 g/l mannose. The best indicator that a plant may be transformed is the observance of active root growth into the medium. Leaf tissue from actively growing plantlets is collected and PCR is done for either the gene of interest or selectable marker before transferring to the green house.

EXAMPLE 3

*Arabidopsis* Transformation

The binary vector pAgroTRIr constructs described in Example 1 above is transformed into *Agrobacterium tumefaciens* strain GV3101 (Bechtold, N. et al., CR Acad. Sci. Paris, Sciences de la vie, 316:1194–1199 (1993)) by electroporation (Dower, W. J., Mol. Biol. Rep 1:5 (1987) A 25 ml culture from single colonies of GV3101 *agrobacterium* containing pAgroTRIr plasmids in YEB+Rifampsin 100 and Kanomycin 100 is incubated at 30 degrees overnight. Large cultures are started by inoculating 500 ml of the same media with 5 mls of the small culture and are incubated overnight at 30 degrees. The OD at 600 nm of cultures is determined and the cultures are then spun down at 5 K in the GSA rotor for 15 minutes. Cells are resuspended in "IM Modified infiltration media" to achieve a final O. D. at 600 nm of 0.08. 200 microliters of Silwet per liter of suspended cells is added. Three pots of bolting *Arabadopsis* var *Columbia* about 4 plants per pot, are inverted in about 500 ml of cell suspension. The flowers are shaken in the cell suspension to dislodge the air bubbles and the plants are incubated in the cell suspension for 15 minutes. A dome is placed on the tray to keep the plants humid overnight.

Plants are allowed to grow about 3–4 weeks after which the plants are not watered for up to 1 week. Seed pods are collected and dried in drying room for about a week and a half. The seeds are planted and allowed to grow for about 2 weeks. The plants are sprayed with the selection agent and then sprayed again 2 days later and 4 days later. After about three days surviving plants can be transplanted to new pots.

EXAMPLE 4

Maize Biolistic Transformation

Type I embryogenic callus cultures (Green et al 1983, Somatic cell genetic systems in corn. A. Fazelahmad, K. Downey, J. Schultz, R W Voellmy, eds. Advances in Gene Technology: Molecular Genetics of Plants and Animals. Miami Winter Symposium Series, Vol.20. Academic Press, NY.) are initiated from immature maize embryos, that are 1.5~2.0 mm in length, from greenhouse grown material. Embryos are aseptically excised from surface-sterilized ears approximately 14 days after pollination. The embryos are placed on D callus initiation media (Duncan et al, (1985) Planta 165:pp322–332) with 2% sucrose and 5 mg/L chloramben. Embryos and embryogenic cultures are subsequently cultured in the dark. Embryogenic responses are excised from the explants after about 14 days. Responses are placed onto D callus maintenance media with 2% sucrose and 0.5 mg/L 2,4-D. After about 6 weeks of weekly selective subculture to fresh maintenance media, high quality compact embryogenic cultures are established. Actively growing embryogenic callus pieces are selected as target tissue for gene delivery. The callus pieces are plated onto target plates containing maintenance medium with 12% sucrose approximately 4 hours prior to gene delivery.

The callus pieces are arranged in circles, with radii of 8 and 10 mm from the center of the target plate.

pNOV1700, described in Example 1 above, is digested with PvuII and XmnI and a 4117 bp fragment comprising a polynucleotide region having a sequence according to SEQ ID NO:1 isolated as well as promoter and polyadenylatin signal. pCIB9818, also described in Example 1 above, is digested with AscI and the 4246 bp fragment comprising the marker gene, promoter and termination signal is isolated. The isolated DNA fragments are precipitated onto gold microcarriers as described in the DuPont Biolistics manual. Two to three µg for each plasmid construct is used in each 6 shot microcarrier preparation. Polynucleotides of the invention are delivered to the target tissue cells using the PDS-1000He Biolistics device. The settings on the Biolistics device are as follows: 8 mm between the rupture disk and the macrocarrier, 10 mm between the macrocarrier and the stopping screen and 7 cm between the stopping screen and the target. Each target plate is shot twice using 650 psi rupture disks. A 200×200 stainless steel mesh (McMaster-Carr, New Brunswick, N.J.) is placed between the stopping screen and the target tissue. Seven days after gene delivery, target tissue pieces are transferred from the high osmotic medium to selection medium.

The target tissue is placed onto maintenance medium containing no sucrose and 1% mannose. After 3 to 5 weeks, growing callus pieces are subcultured to the maintenance medium containing no sucrose and 1.5% mannose. Embryogenic callus growing on selection media is subcultured every 2 weeks for 6 to 10 weeks until enough callus is produced to generate 10–20 plants. Tissue surviving selection from an original target tissue piece is subcultured as a single colony and designated as an independent transformation event. Colonies are transferred to a modified MS medium (Murashige and Skoog, 1962(1962) A revised medium for rapid growth and bioassays with tobacco tissue cultures. Physiol. Plant 15: 473–497.) containing 2% sucrose and 1% mannose (MS2S+1M) with 0.25 mg/L ancymidol and 0.5 mg/L. kinetin. After 2 weeks, regenerating colonies are then transferred to MS2S+1M without hormones. Regenerating shoots with or without roots from all colonies are transferred to Magenta boxes containing MS3S medium and small plants with roots are recovered and transferred to soil in the greenhouse.

EXAMPLE 5

Analyses of Transgenic Plant Expression

Tissue from transformed plants is analyzed for the presence of a polynucleotide comprising the sequence of SEQ ID NO:1. DNA is extracted from transformed plant and PCR analyses are performed according to standard protocols. The primers used for amplification of the gene constructs are (5'-acgaatcattcaccgaggag-3') (SEQ ID No. 3) and (5'-ctcacactctcaggcttacc-3') (SEQ ID NO. 4). A 650 nt fragment within the sequence of SEQ ID NO:1 in wheat obtained according to Example 2 above is detected.

b. Northern Analysis

Transformed plants are analyzed for the presence of RNA by northern blot hybridization. For northern blot analysis, RNA extracted from plant tissue is size separated and blotted onto a nylon membrane. This membrane is subsequently hybridized with a radioactive probe, derived from the 429 nt StyI fragment of the polynucleotide according to SEQ ID NO:1 is used as the probe. RNA is detected in wheat and *arabadopsis* plants transformed according to examples 2 and 3 above.

EXAMPLE 6

Enzymatic Assay for Trichothecene 3-O-acetyltransferase Activity 1. a.) Extraction of plant tissue for enzyme assays: Three 1×⅛ in pieces of leaf (about 50 mg) from transgenic plants of the invention including those transformed and regenerated according to Examples 2–4 above are selected.

(b) Glass Bead Mill: Tissue is placed in 2 ml round bottomed tube and the cap closed. The tube is immersed in liquid nitrogen and is incubated overnight at ~80° C. Tube is shaken on saws-all 24 seconds and 0.4 ml sodium phosphate buffer is added. The tube is vortexed about 10 seconds and is placed on ice. The tube is vortexed another 5 minutes and then is spun at 14,000 rpm in Eppendorf centrifuge 5 min. The supernatant is removed and is placed in a clean tube.

2. a) The following components are mixed trichothecene substrate, 2 microliters of DAS (20% acetone in 50 mM Sodium phosphate buffer pH 7.0). DON may also be used.

Acetyl CoA substrate, 2 micro liters of [$^{14}$C]-acetyl CoA NEN cat. #NEC313 (60 mCi/millimole and 0.02 mCi/ml)

Buffer, to a final volume of 50 μl with sodium phospahate buffer pH 7.0 b) The assay is initiated by adding the following enzyme preparation and is incubated at 30° C. for 15 minutes.

Enzyme preparation, 10 microliter plant extract in sodium phosphate buffer pH 7.0 c) After 15 minutes, 100 microliters ethyl acetate is added and the tube is vortexed twice for several seconds. The tube is spun for 2 minutes at 14,000 rpm in an Eppendorf centrifuge. 50 microliters of the ethyl acetate phase is removed and is added to a vial containing scintillation cocktail. The tube is counted for 2 min. using a scintillation counter.

Twenty separate wheat plants obtained according to Example 2 above and having specific activities of 0.60 to 13.4 nmol acetylated product/ug protein/15 min are identified. The specific activities of the transformed wheat plants are significantly greater than the negative control. The negative control is a non-transformed wheat cultivar, which has a specific activity of 0.1 to 0.2 nmol acetylated product/ug protein/15 min.

Five separate *Arabidopsis* plants obtained according to Example 3 above and having specific activities ranging from 3.8 to 28 mmol acetylated product/ug protein/15 min are identified. The specific activities of the transformed plants are significantly greater than that of the negative control. The negative control is an *Arabidopsis thaliana* var *columbia* transformed with a nucleic acid construct for expressing the selectable marker which has a specific activity of less than 0.1 nmol acetylated product/ug protein/15 min.

Maize plants from at least two different transformants obtained according to Example 4 above and having specific activities ranging from 11.1 to 17.9 nmol acetylated product/ug protein/15 min are identified. The specific activities of the transformed plants are significantly greater than that of the negative control. The negative control is a non-transformed maize genotype that has a specific activity of less than 0.2 nmol acetylated product/ug protein/15 min.

Maize plants from at least 16 different transformants obtained using *Agrobacterium* mediated transformation of pNOV 1704, having specific activities ranging from 17 to 183 nmol/microgram/15 min are identified.

EXAMPLE 7

Bioassay for Trichothecene Resistance in Transgenic Plants 250 ml of CPR media having the following components is prepared and the pH adjusted to 6.5 with KOH.

| | |
|---|---|
| ½ MS salts | 0.54 g |
| ½ MS vitamins | 1.25 ml |
| Sucrose 1% (optional) | 2.50 g |

Agarose is added to the above media to a concentration of 1% (2.50 g) and the media is autoclaved. 25 ml of 50 mg/ml chlorophenol red is added to the autoclaved media. While media is maintained at 55° C., DAS or DON is added in acetone at various concentrations. (i.e. DON at 4, 8, or 16 microliters 10 mg/ml or DAS at 2, 4, or 6 microliters 50 mg/ml DAS per 1.7 ml). About 0.5 ml of media is aliquoted to each well in a 48 well microtiter plate.

⅓×⅛ inch pieces of transformed plant tissue are added to microtiter plate wells as well as control tissue from untransformed wild type controls. The leaf pieces are allowed to fall into a petri dish and are pushed into the microtiter plate well media with tweezers. The microtiter plates are incubated 2 to 4 days at 20° C. under lights. Leaf piece metabolism results in color change (drop in pH) from red to yellow. Trichothecene resistance activity or reduced sensitivity to trichothecenes by transformants, results in yellow colored wells in the presence of DAS or DON.

A color change from red to yellow compared to the control that remains red is observed in wheat and maize plants of the invention. Furthermore, the individual leaf pieces have significantly less chlorosis than the corresponding control.

EXAMPLE 8

Germination Assay

A. Trichothecene Resistance Germination Assay

Seed from transgenic plants of the invention is grown under selective pressure from the selection agent and the resulting plants are selfed. The resulting seed is plated on MS3S medium (MS salts 4.3 g/L, MS vitamins 100X, Sucrose 30 g/L, and phytagar 8 g/L) and supplemented with either DAS or DON (at 20 mg/ml) at a density of 1000 to 1200 seeds/petri dish (100 mm diameter). After incubation in the light for four days the plates are examined for seedling growth.

Arabidopsis seed from plants obtained according to Example 3 above and grown in media comprising DAS, has numerous plants with both root and shoot development. While control seed (parental *Arabadopsis* line, var.*Columbia*) germinates poorly and no roots form when grown in DAS supplemented media. No differences are observed between transformed and control seeds grown in the same media without DAS.

B. Fungal Resistance Germination Assay for Detecting Resistance to Seedling Blight 1. Wheat Fungal Resistance Germination Assay:

Fungal resistance germination assays in wheat are carried out substantially as described by R. H. Proctor, T. M. Hohn, and S. P. McCormick. Reduced virulence of *Gibberella zeae* caused by disruption of a trichothecene toxin biosynthetic gene. *Mol. Plant-Microbe Interact.* 8 (4):593–601, 1995.) which is herein incorporated by reference in its entirety.

Inoculum consists of macroconidia of *F. gramiearum* diluted in water to $1\times10^6$ conidia per ml. Inoculum is prepared by washing the macroconidia from V-8 juice agar cultures grown under white and near UV fluorescent lights for 7–10 days. In seedling assays, seeds of two different transgenic wheat events from Example 2 above and the wild type control are surface sterilized by washing in a 10% bleach and 0.05% Tween solution for approximately 15 min. and rinsed five times with sterile distilled water. The seeds are soaked in a suspension of macroconidia for approximately 10 min and then sown in vermiculite contained in 10 cm plastic pots (20 seeds per pot). Prior to sowing, the pots are filled approximately ¾ full with vermiculite and set in 2–4 cm of water until the top of the vermiculite was wet. After sowing, seeds are covered with an additional 1–2 cm of vermiculite and pots are placed individually into plastic bags and incubated in a growth chamber at 22° C. with 16 h light and 8 h dark for week. After approximately one week the pots are removed from the bags, and after two weeks, disease is evaluated by counting the number of seedlings that emerge in each pot. Controls are treated as described above except that the seeds are soaked in sterile water and 40 seeds are used.

50% and 43% of the seed from the two different transgenic plant events germinate as compared to the same transgenic seed treated with water, whereas, 17% of the wild type control germinate compared to the same seed treated with water.

2. Maize Fungal Resistance Germination Assay:

Inoculum is produced from *F. graminearum* cultures grown on mung bean agar (made with liquor from boiled mung beans) under 12 h alternating light and dark cycles at 25° C. Spores are harvested by first flooding the plate with sterile water and then scraping the plate using a glass rod. The solution is collected and the spore concentration adjusted to 1×106 spores/ml with double distilled, sterile water on the day of inoculation.

Soil consisting of a sterilized mix of soil, peat, and vermiculite is inoculated with 1 ml of spore solution/liter of soil in 5 liter flats and the inoculated soil is mixed in a cement mixer for 2 minutes per load. Control treatments consist of non-infested soil. Flats are planted with 30 kernels each of the transgenic seed of the invention or wild type control and incubated in growth chambers kept at 55° F. under semi-saturated soil conditions for up to 4 weeks. Light levels are under 24-hour darkness for 14 days post planting, and 12-hour light 15–24 days post planting. Labeled stakes are added to flats, flats are moved to the growth chamber and randomized.

Plant counts are initiated as soon as emergence begins, and are performed daily or every other day until there is no longer a change in plant emergence.

Symptoms of visual discoloration and damping-off of seedling emergence are determined and used to characterize the degree of plant resistance as compared to wild type controls. Plants having less visual discoloration and/or damping off of seedling emergence than the wild type control are selected.

EXAMPLE 9

Fungal Resistance Assay

A. Testing of Transgenic Wheat Plants

Wheat head blight or head scab is caused by *Fusarium graminearum* (teleomorph: *Gibberella zeae*). *F. graminearum* cultures are grown on V-8 agar medium (made with V-8 juice) or on mung bean agar (made with liquor from boiled mung beans) under 12 h alternating light and dark cycles at 25° C. Spores are harvested by first flooding the plate with sterile water and then scraping the plate using a glass rod. The solution is collected and the spore concentration adjusted to $5\times10^4$ spores/ml with double distilled, sterile water on the day of inoculation.

Transgenic plants are obtained as described in Example 2 above, and control plants may be grown in the greenhouse until anthesis or heading. Heads are inoculated by injecting approximately 20 ul (about 1000 spores) of inoculum between the lemma and palea of one floret near the middle of each head. Some heads are left uninoculated or are inoculated with sterile water as controls. Plants are then moved to a growth chamber and incubated under high humidity for up to 21 days or plants are first incubated in a mist chamber for 72 h at 65 to 70° F. and then incubated in the greenhouse for an additional 18 days.

Transgenic plants of the invention and control plant may also be grown in the field, where heads are inoculated by spraying.

Disease is evaluated by counting the number of symptomatic and asymptomatic spikelets on each inoculated head on a representative number of transgenic heads and wild type control heads and from this calculating the percentage of spikelets on each head that are symptomatic. Symptoms consist of premature whitening as compared to the control plants and in some cases necrosis of spikelets. Plants having fewer symptomatic spikelets than the wild type control are selected.

Six different transgenic plants having different copy numbers of SEQ ID NO.1 and different numbers of insertion sites according to southern data have average percent of symptomatic spikelets per head ranging from 10.40% to 31.20% compared to 44.75% for the wild type control, where the transgenic plants and controls are incubated in the green house as described above. These same transgenic plants have enzymatic activities, measured as described in example 6 above, ranging from 0.874 to 29.1 nmol/microgram/15 min.

B. Testing of Transgenic Corn Plants

Corn Ear Rot Assay.

Corn ear rot is caused by *Fusarium graminearum* (teleomorph: *Gibberella zeae*). *F. graminearum* cultures are grown on V-8 agar medium (made with V-8 juice) under 12 h alternating light and dark cycles at 25° C. Spores are harvested by first flooding the plate with sterile water and then scraping the plate using a glass rod. The solution is collected and the spore concentration adjusted to 5×10$^5$ spores/ml with double distilled, sterile water) on the day of inoculation. Transgenic plants and control plants are grown in the greenhouse or field. Where grown in the greenhouse, the transgenic and control plants are maintained in the green house until four to seven days post silk emergence when a 2 ml spore suspension is introduced into the silk channel (inside the husk cavity and above the cob). This is accomplished using an 18-gauge stainless steel hypodermic needle attached to a large syringe. In addition to silk channel inoculations, a kernel inoculation method is also used to assay disease resistance. Kernel inoculation involves the introduction of the spore suspension (approx. 0.4 ml) into a group of four kernels through multiple injections with an 18-gauge needle attached to a syringe. Disease is evaluated by visual inspection of ears harvested 5 to 7 weeks post-inoculation for visibly infected kernels. The disease rating scale for husked ears is based on a visual estimation of the percentage of visibly infected kernels on an ear as follows: 1 is 0%; 2 is 1 to 3%; 3 is 4 to 10%; 4 is 11 to 25%; 5 is 26 to 50%; 6 is 51 to 75%; 7 is 76 to 100%. Maize plants are selected that have a lower percentage of visibly infected kernels compared to the wild type control.

EXAMPLE 10

Mycotoxin Contamination Assay

Samples are prepared for mycotoxin concentration analysis as follows. Seed is collected from transgenic plants of the invention weighed and bulked together. Where wheat seed is being assayed, wheat seed is collected from the heads of the same transgenic plants of the invention and weighed and bulked together. Where transgenic maize is being assayed, corn ears are dried to low moisture levels, ears are hand-shelled and kernels from ears of the same transgenic plant are weighed and bulked together. Each seed or kernel sample is mixed thoroughly to promote a random distribution of seed. A 50 g seed or kernel sample is ground to a fine powder in a mill (e.g. Retsch ultra centrifugal mill type ZM1, BrinkmanInstruments, Inc., Rexdale, Ontario, Romer Series II Mill, Union, Mo., USA). The concentration of the mycotoxin of interest such as, DON is then determined using the commercially available tests such as DONtest TAG™ mycotoxin testing system (VICAM, LP, 313 Pleasant Street, Watertown, Mass. 02472) or analyzed by a commercial analysis company (e.g. Romer Labs, Inc, Union, Mo., USA or Trilogy Analytical Laboratory, Inc., Beaufort, Mo., USA). The manufacturer's instructions are followed for all aspects of the analysis. For DONtest TAG™ mycotoxin testing system, a final fluorometric measurement for DON is conducted. Plants producing seed or kernels having less mycotoxin, such as DON, than the wild type control are selected.

Example 11

Use of Polynucleotide According to SEQ ID NO:1 as a Selectable Marker

A. Selectable Marker in Fungal Cells.

Ashbya gossypi is transformed using standard fungal transformation techniques with a DNA construct comprising a polynucleotide having the sequence of SEQ ID NO:1 operably linked to the galactosidase promoter. Transformed cells grow in media comprising DAS at a concentration ranging from 1.56 ng/ml to 196 pg/ml whereas as the untransformed wild type fungal cells do not.

B. Selectable Marker in Plant Cells.

Seed from Arabidopsis plants transformed according to Example 3 above but not yet subjected to selection is plated out in 0.1% agarose medium containing 0, 5, or 10 ug/ml DAS. After incubation in a growth room at 22 C with 16 hours of light and 8 hours of darkness for 2 weeks, the larger unstunted plants are transplanted from a DAS plate, and a corresponding number are transplanted from the control plate.

Leaves of Arabidopsis plants transplanted from the 5 microgram/ml plate, are assayed for enzymatic activity after a 2 week growth period, and showed 11 out of 11 unstunted plants were enzymatically active as measured by Example 6 while 9 out of 10 plants not selected by DAS were negative in the same assay. The one non-selected plant that was enzymatically active was much less active than any of the DAS selected plants assayed.

The above-disclosed embodiments are illustrative. This disclosure of the invention will place one skilled in the art in possession of many variations of the invention. All such obvious and foreseeable variations are intended to be encompassed by the appended claims.

What is claimed is:

1. An isolated nucleic acid molecule comprising a nucleotide sequence that encodes SEQ ID NO: 6.

2. The isolated nucleic acid molecule of claim 1, wherein said nucleic acid molecule comprises the nucleotide sequence set forth in SEQ ID NO: 5.

3. A chimeric DNA comprising a heterologous promoter sequence operably linked to the nucleic acid molecule of claim 1.

4. A recombinant vector comprising the chimeric DNA of claim 3.

5. A transgenic host cell comprising the chimeric DNA of claim 3.

* * * * *

SEQUENCE LISTING

```
<160> NUMBER OF SEQ ID NOS: 11

<210> SEQ ID NO 1
<211> LENGTH: 1403
<212> TYPE: DNA
<213> ORGANISM: Fusarium sporotrichioides

<400> SEQUENCE: 1
atcaaaatgg ccgcaacaag cagcacaagc agccagtctt ttgacataga gctcgacatc      60
atcggccagc aaccgcctct tctttcaatc tacacccaga tcagtctcgt ttaccccgtc     120
tctgatccct cccagtatcc caccatcgtc agcacccttg aggaaggcct aaaacgcctc     180
tctcaaacct tcccatgggt cgcgggccag gtcaagaccg agggcatcag cgaaggaaac     240
```

-continued

```
acaggaactt ccaagatcat tccatatgag gagacacccc gtcttgtggt gaaagacctc    300
cgtgatgatt cctcagcgcc aacgatcgag gggttgagaa aggcgggttt ccccttagag    360
atgtttgacg agaacgtcgt cgctccgagg aagacattag ctatcggacc tggcaatggc    420
cccaacgacc cgaagcctgt gttgctattg cagctcaact tcattaaggg cggactcatt    480
ctcaccgtca acggacaaca tggtgctatg gacatgacag gacaagatgc aattattcgt    540
cttctctcca aggcgtgccg caacgaatca ttcaccgagg aggaaatctc ggccatgaac    600
ctcgatcgca agacggtagt ccctctcctt gaaaactaca agttggtcc tgagctagac    660
caccagatcg ccaaacctgc gcctgctggc gacgctccac ccgcaccggc caaggcaagc    720
tgggcgttct tttcattcac tcccaaggcc ctctcggagc tgaaagacgc agccacaaag    780
actcttgacg cgtcgtccaa gtttgtgtca actgatgatg ctctttcggc gtttatctgg    840
caatcaacct cgcgcgtacg tctcgcaaga ttggatgctt ccacacctac tgaattctgc    900
cgcgctgtcg acatgcgggg cccaatgggc gtatcaagca catcccagg ccttcttcaa    960
aacatgacct accatgactc gaccgtcgcc gaaatcgcca acgaaccact ggcgcaaca   1020
gcatcacgcc tgcgctcgga actcaacagt gatcgtttgc gcagacgaac acaagctttg   1080
gcgacgtaca tgcatggcct gcctgacaag tcgagcgtct ccctgaccgc cgatgcgaat   1140
ccgtcaagca gcatcatgct gagttcctgg gccaaggtgg gatgctggga gtatgacttt   1200
gggtttggac tgggtaagcc tgagagtgtg agaagacctc gctttgaacc ttttgagagt   1260
ttgatgtact ttatgcccaa gaagcctgat ggggagttta cggcgtccat ttctctgagg   1320
gatgaggata tggagagact aaaggcggat gaggagtgga caaagtacgc aaagtatatt   1380
gggtagatag tttactagac tac                                          1403
```

<210> SEQ ID NO 2
<211> LENGTH: 459
<212> TYPE: PRT
<213> ORGANISM: Fusarium sporotrichioides

<400> SEQUENCE: 2

```
Met Ala Ala Thr Ser Ser Thr Ser Ser Gln Ser Phe Asp Ile Glu Leu
1               5                   10                  15

Asp Ile Ile Gly Gln Gln Pro Pro Leu Leu Ser Ile Tyr Thr Gln Ile
            20                  25                  30

Ser Leu Val Tyr Pro Val Ser Asp Pro Ser Gln Tyr Pro Thr Ile Val
        35                  40                  45

Ser Thr Leu Glu Glu Gly Leu Lys Arg Leu Ser Gln Thr Phe Pro Trp
    50                  55                  60

Val Ala Gly Gln Val Lys Thr Glu Gly Ile Ser Glu Gly Asn Thr Gly
65                  70                  75                  80

Thr Ser Lys Ile Ile Pro Tyr Glu Glu Thr Pro Arg Leu Val Val Lys
                85                  90                  95

Asp Leu Arg Asp Asp Ser Ser Ala Pro Thr Ile Glu Gly Leu Arg Lys
            100                 105                 110

Ala Gly Phe Pro Leu Glu Met Phe Asp Glu Asn Val Val Ala Pro Arg
        115                 120                 125

Lys Thr Leu Ala Ile Gly Pro Gly Asn Gly Pro Asn Asp Pro Lys Pro
    130                 135                 140

Val Leu Leu Leu Gln Leu Asn Phe Ile Lys Gly Gly Leu Ile Leu Thr
145                 150                 155                 160
```

-continued

```
Val Asn Gly Gln His Gly Ala Met Asp Met Thr Gly Gln Asp Ala Ile
            165                 170                 175
Ile Arg Leu Leu Ser Lys Ala Cys Arg Asn Glu Ser Phe Thr Glu Glu
        180                 185                 190
Glu Ile Ser Ala Met Asn Leu Asp Arg Lys Thr Val Val Pro Leu Leu
    195                 200                 205
Glu Asn Tyr Lys Val Gly Pro Glu Leu Asp His Gln Ile Ala Lys Pro
210                 215                 220
Ala Pro Ala Gly Asp Ala Pro Pro Ala Pro Lys Ala Ser Trp Ala
225                 230                 235                 240
Phe Phe Ser Phe Thr Pro Lys Ala Leu Ser Glu Leu Lys Asp Ala Ala
                245                 250                 255
Thr Lys Thr Leu Asp Ala Ser Ser Lys Phe Val Ser Thr Asp Asp Ala
            260                 265                 270
Leu Ser Ala Phe Ile Trp Gln Ser Thr Ser Arg Val Arg Leu Ala Arg
        275                 280                 285
Leu Asp Ala Ser Thr Pro Thr Glu Phe Cys Arg Ala Val Asp Met Arg
    290                 295                 300
Gly Pro Met Gly Val Ser Ser Thr Tyr Pro Gly Leu Leu Gln Asn Met
305                 310                 315                 320
Thr Tyr His Asp Ser Thr Val Ala Glu Ile Ala Asn Glu Pro Leu Gly
                325                 330                 335
Ala Thr Ala Ser Arg Leu Arg Ser Glu Leu Asn Ser Asp Arg Leu Arg
            340                 345                 350
Arg Arg Thr Gln Ala Leu Ala Thr Tyr Met His Gly Leu Pro Asp Lys
        355                 360                 365
Ser Ser Val Ser Leu Thr Ala Asp Ala Asn Pro Ser Ser Ser Ile Met
    370                 375                 380
Leu Ser Ser Trp Ala Lys Val Gly Cys Trp Glu Tyr Asp Phe Gly Phe
385                 390                 395                 400
Gly Leu Gly Lys Pro Glu Ser Val Arg Arg Pro Arg Phe Glu Pro Phe
                405                 410                 415
Glu Ser Leu Met Tyr Phe Met Pro Lys Lys Pro Asp Gly Glu Phe Thr
            420                 425                 430
Ala Ser Ile Ser Leu Arg Asp Glu Asp Met Glu Arg Leu Lys Ala Asp
        435                 440                 445
Glu Glu Trp Thr Lys Tyr Ala Lys Tyr Ile Gly
    450                 455
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: DNA Primer

<400> SEQUENCE: 3
acgaatcatt caccgaggag                                        20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: DNA Primer

<400> SEQUENCE: 4

-continued

```
ctcacactct caggcttacc                                                    20

<210> SEQ ID NO 5
<211> LENGTH: 1356
<212> TYPE: DNA
<213> ORGANISM: Fusarium graminearum

<400> SEQUENCE: 5
atggctttca agatacagct cgacaccctc ggccagctac caggcctcct ttcgatctac      60
acccaaatca gtctcctcta ccccgtctct gattcctctc aatatcccac tattgtcagc     120
accttcgagc aaggtcttaa gcgcttctcc gaagccgtcc catgggtcgc aggccaggtc     180
aaagccgagg gcattagcga gggaaacaca ggaacttcct ttatcgtccc ttttgaggac     240
gttcctcgtg ttgtagtgaa agacctccgc gatgatcctt cagcgcccac gatcgagggt     300
atgagaaagg cgggataccc tatggcgatg tttgacgaga acatcatcgc gccaaggaag     360
acgttaccta ttggacctgg tactggtccc gacgacccaa agcctgtaat tctattgcag     420
ctcaacttca tcaagggcgg actcatcctc actgtcaacg gacagcacgg tgctatggat     480
atggtaggcc aagatgcggt gatccgtcta ctctccaagg cgtgccgtaa cgacccattc     540
accgaagagg aaatgacggc catgaacctc gatcgcaaga cgatagttcc ttaccttgaa     600
aactatacga ttggccccga ggtagatcat cagattgtca aagctgatgt agctggtggt     660
gacgctgttc tcacgccggt cagtgcaagc tgggcgttct tcacattcag ccccaaggcc     720
atgtcagagc tcaaggatgc tgctaccaag actcttgacg catcaacaaa gttcgtgtcg     780
actgacgatg ctctttcggc gttcatctgg aaatcggcct ctcgcgtgcg tctcgaaaga     840
atcgatggct ctgcacctac cgagttctgc cgtgctgttg atgctcgacc ggcaatgggt     900
gtctcgaaca actacccagg ccttcttcaa aacatgacct accacaactc gaccatcggc     960
gaaatcgcca acgagtcact cggcgcaaca gcatcacgcc ttcgttcaga actcgacccc    1020
gcgagcatgc gccagcgaac aagaggtctc gcgacgtacc tgcacaacaa ccccgacaag    1080
tccaacgtat ccctgacggc tgatgcggac ccatctacca gcgtcatgct gagttcttgg    1140
gccaaggtgg gactctggga ttacgacttt gggctcggac tgggtaagcc cgagactgtg    1200
agacggccaa tctttgagcc tgttgagagc ttgatgtact ttatgcccaa gaagcctgat    1260
ggcgagttct gtgcggcgct ttctctgagg gatgaggata tggaccgatt gaaggcggat    1320
aaggagtgga ccaagtatgc gcagtacgtt ggttag                              1356

<210> SEQ ID NO 6
<211> LENGTH: 451
<212> TYPE: PRT
<213> ORGANISM: Fusarium graminearum

<400> SEQUENCE: 6

Met Ala Phe Lys Ile Gln Leu Asp Thr Leu Gly Gln Leu Pro Gly Leu
1               5                   10                  15

Leu Ser Ile Tyr Thr Gln Ile Ser Leu Leu Tyr Pro Val Ser Asp Ser
            20                  25                  30

Ser Gln Tyr Pro Thr Ile Val Ser Thr Phe Glu Gln Gly Leu Lys Arg
        35                  40                  45

Phe Ser Glu Ala Val Pro Trp Val Ala Gly Gln Val Lys Ala Glu Gly
    50                  55                  60

Ile Ser Glu Gly Asn Thr Gly Thr Ser Phe Ile Val Pro Phe Glu Asp
65                  70                  75                  80
```

-continued

Val Pro Arg Val Val Lys Asp Leu Arg Asp Pro Ser Ala Pro
            85                  90                  95

Thr Ile Glu Gly Met Arg Lys Ala Gly Tyr Pro Met Ala Met Phe Asp
                100                 105                 110

Glu Asn Ile Ile Ala Pro Arg Lys Thr Leu Pro Ile Gly Pro Gly Thr
            115                 120                 125

Gly Pro Asp Asp Pro Lys Pro Val Ile Leu Leu Gln Leu Asn Phe Ile
130                 135                 140

Lys Gly Gly Leu Ile Leu Thr Val Asn Gly Gln His Gly Ala Met Asp
145                 150                 155                 160

Met Val Gly Gln Asp Ala Val Ile Arg Leu Leu Ser Lys Ala Cys Arg
                165                 170                 175

Asn Asp Pro Phe Thr Glu Glu Met Thr Ala Met Asn Leu Asp Arg
            180                 185                 190

Lys Thr Ile Val Pro Tyr Leu Glu Asn Tyr Thr Ile Gly Pro Glu Val
            195                 200                 205

Asp His Gln Ile Val Lys Ala Asp Val Ala Gly Gly Asp Ala Val Leu
            210                 215                 220

Thr Pro Val Ser Ala Ser Trp Ala Phe Phe Thr Phe Ser Pro Lys Ala
225                 230                 235                 240

Met Ser Glu Leu Lys Asp Ala Ala Thr Lys Thr Leu Asp Ala Ser Thr
                245                 250                 255

Lys Phe Val Ser Thr Asp Asp Ala Leu Ser Ala Phe Ile Trp Lys Ser
            260                 265                 270

Ala Ser Arg Val Arg Leu Glu Arg Ile Asp Gly Ser Ala Pro Thr Glu
            275                 280                 285

Phe Cys Arg Ala Val Asp Ala Arg Pro Ala Met Gly Val Ser Asn Asn
290                 295                 300

Tyr Pro Gly Leu Leu Gln Asn Met Thr Tyr His Asn Ser Thr Ile Gly
305                 310                 315                 320

Glu Ile Ala Asn Glu Ser Leu Gly Ala Thr Ala Ser Arg Leu Arg Ser
                325                 330                 335

Glu Leu Asp Pro Ala Ser Met Arg Gln Arg Thr Arg Gly Leu Ala Thr
            340                 345                 350

Tyr Leu His Asn Asn Pro Asp Lys Ser Asn Val Ser Leu Thr Ala Asp
            355                 360                 365

Ala Asp Pro Ser Thr Ser Val Met Leu Ser Ser Trp Ala Lys Val Gly
370                 375                 380

Leu Trp Asp Tyr Asp Phe Gly Leu Gly Leu Gly Lys Pro Glu Thr Val
385                 390                 395                 400

Arg Arg Pro Ile Phe Glu Pro Val Glu Ser Leu Met Tyr Phe Met Pro
                405                 410                 415

Lys Lys Pro Asp Gly Glu Phe Cys Ala Ala Leu Ser Leu Arg Asp Glu
            420                 425                 430

Asp Met Asp Arg Leu Lys Ala Asp Lys Glu Trp Thr Lys Tyr Ala Gln
            435                 440                 445

Tyr Val Gly
    450

<210> SEQ ID NO 7
<211> LENGTH: 1425
<212> TYPE: DNA
<213> ORGANISM: Saccharomyces cerevisiae

<400> SEQUENCE: 7

```
atgtttagag tcaagatcat ctctcagaaa cgtacaaaaa gtgtacagat gctagaaaac    60
gatcaacttg atattttggg acaacaacct tcgctataca aactatacac tcaaatatgc   120
tctatctacc gtgtaccaga tccttctgct catgaccata tcgtaaatac cttaacaaga   180
ggacttgaaa cattggctaa aaatttccag tggctagcag gaaatgtcgt aaatgaaggt   240
gctgacgaag gtaacactgg tacctacaga attgtcccgt cagacaaaat tccacttatc   300
gtccaagatc ttcgagaaga tctgtctgcc ccaacaatgg attcgcttga aaaagctgac   360
tttcctatct acatgttaga cgaaaagact tttgcgcctt gcatgactat caatccacct   420
ggaaacacta taggtatggc cgccaagagt gggcctgtat ttgcagttca agcaaacttt   480
atctccggcg gcctcgtctt aactattgtc gggcagcaca atattatgga tataacagga   540
caggaaagta tcatcaactt gctcaataaa tcttgccacc aaaaaccttt ctctgatgaa   600
gaactgctca ttggaaatat agataaaagc aaatctattc ctttgtttga tgaaacttgg   660
gaacccgaca ccacgctagt tcatgaaata gtggaaacct ctagaaatac aagtggagag   720
gaaaaggaac agtcttgttc ttcgaactct acttgggctt atgttgaatt ttctgctatc   780
tcattgcaga atctgaggat tttggcaatg cagacatgta cttctggcac aaaatttgtc   840
tccactgatg atatcgtcac tgctttcatc tggaaatcag tttctcgagc ccgtttatct   900
cgacttaaac cagaaacgaa atcaaattta gggcgtgctg tggatgttag aaaacggcta   960
ggactccccg aaacgtatcc agggttatta gtcaacatga cctttaatac aggttccctg  1020
aaaagcttgg atcataaaag tttgggcgtt cttgcatcac agattcgcag gaagctagac  1080
cctaaagtct tcgatttggc ctataataca tgcgcacttg ctacgctcct tagccgatgc  1140
ccggacaaga ctaaggtttc tatacctcaa ccaattgata ctttatctgg aattatggtc  1200
agttcgtggg caaaagtcag cctgtatgac gttgatttca atctagggct tgggaagccc  1260
aagagtgtac gacggccgcg cttcatttcc cttgagagcc taatatattt tatgcctaga  1320
tcctccagag gtgaaatggt ggttgctctt tgccttagag ataaagattg ggagtgcctg  1380
aatgcggata agaatggaca aaattatgct acacatatag gatga                  1425
```

<210> SEQ ID NO 8
<211> LENGTH: 474
<212> TYPE: PRT
<213> ORGANISM: Saccharomyces cerevisiae

<400> SEQUENCE: 8

Met Phe Arg Val Lys Ile Ile Ser Gln Lys Arg Thr Lys Ser Val Gln
1               5                   10                  15

Met Leu Glu Asn Asp Gln Leu Asp Ile Leu Gly Gln Gln Pro Ser Leu
            20                  25                  30

Tyr Lys Leu Tyr Thr Gln Ile Cys Ser Ile Tyr Arg Val Pro Asp Pro
        35                  40                  45

Ser Ala His Asp His Ile Val Asn Thr Leu Thr Arg Gly Leu Glu Thr
    50                  55                  60

Leu Ala Lys Asn Phe Gln Trp Leu Ala Gly Asn Val Val Asn Glu Gly
65                  70                  75                  80

Ala Asp Glu Gly Asn Thr Gly Thr Tyr Arg Ile Val Pro Ser Asp Lys
                85                  90                  95

Ile Pro Leu Ile Val Gln Asp Leu Arg Glu Asp Leu Ser Ala Pro Thr
            100                 105                 110

Met Asp Ser Leu Glu Lys Ala Asp Phe Pro Ile Tyr Met Leu Asp Glu

```
            115                 120                 125
Lys Thr Phe Ala Pro Cys Met Thr Ile Asn Pro Gly Asn Thr Ile
130                 135                 140

Gly Met Ala Ala Lys Ser Gly Pro Val Phe Ala Val Gln Ala Asn Phe
145                 150                 155                 160

Ile Ser Gly Gly Leu Val Leu Thr Ile Val Gly Gln His Asn Ile Met
                165                 170                 175

Asp Ile Thr Gly Gln Glu Ser Ile Ile Asn Leu Leu Asn Lys Ser Cys
            180                 185                 190

His Gln Lys Pro Phe Ser Asp Glu Glu Leu Leu Ile Gly Asn Ile Asp
        195                 200                 205

Lys Ser Lys Ser Ile Pro Leu Phe Asp Glu Thr Trp Glu Pro Asp Thr
210                 215                 220

Thr Leu Val His Glu Ile Val Glu Thr Ser Arg Asn Thr Ser Gly Glu
225                 230                 235                 240

Glu Lys Glu Gln Ser Cys Ser Ser Asn Ser Thr Trp Ala Tyr Val Glu
                245                 250                 255

Phe Ser Ala Ile Ser Leu Gln Asn Leu Arg Ile Leu Ala Met Gln Thr
            260                 265                 270

Cys Thr Ser Gly Thr Lys Phe Val Ser Thr Asp Asp Ile Val Thr Ala
        275                 280                 285

Phe Ile Trp Lys Ser Val Ser Arg Ala Arg Leu Ser Arg Leu Lys Pro
290                 295                 300

Glu Thr Lys Ser Asn Leu Gly Arg Ala Val Asp Val Arg Lys Arg Leu
305                 310                 315                 320

Gly Leu Pro Glu Thr Tyr Pro Gly Leu Leu Val Asn Met Thr Phe Asn
                325                 330                 335

Thr Gly Ser Leu Lys Ser Leu Asp His Lys Ser Leu Gly Val Leu Ala
            340                 345                 350

Ser Gln Ile Arg Arg Lys Leu Asp Pro Lys Val Phe Asp Leu Ala Tyr
        355                 360                 365

Asn Thr Cys Ala Leu Ala Thr Leu Leu Ser Arg Cys Pro Asp Lys Thr
370                 375                 380

Lys Val Ser Ile Pro Gln Pro Ile Asp Thr Leu Ser Gly Ile Met Val
385                 390                 395                 400

Ser Ser Trp Ala Lys Val Ser Leu Tyr Asp Val Asp Phe Asn Leu Gly
                405                 410                 415

Leu Gly Lys Pro Lys Ser Val Arg Arg Pro Arg Phe Ile Ser Leu Glu
            420                 425                 430

Ser Leu Ile Tyr Phe Met Pro Arg Ser Ser Arg Gly Glu Met Val Val
        435                 440                 445

Ala Leu Cys Leu Arg Asp Lys Asp Trp Glu Cys Leu Asn Ala Asp Lys
450                 455                 460

Glu Trp Thr Asn Tyr Ala Thr His Ile Gly
465                 470

<210> SEQ ID NO 9
<211> LENGTH: 6111
<212> TYPE: DNA
<213> ORGANISM: Plasmid

<400> SEQUENCE: 9
aagcttgcat gcctgcagtg cagcgtgacc cggtcgtgcc cctctctaga gataatgagc    60
attgcatgtc taagttataa aaaattacca catattttt ttgtcacact tgtttgaagt   120
```

-continued

```
gcagtttatc tatctttata catatattta aactttactc tacgaataat ataatctata      180
gtactacaat aatatcagtg ttttagagaa tcatataaat gaacagttag acatggtcta      240
aaggacaatt gagtattttg acaacaggac tctacagttt tatctttta gtgtgcatgt      300
gttctccttt tttttgcaa atagcttcac ctatataata cttcatccat tttattagta      360
catccatta gggtttaggg ttaatggttt tatagacta attttttag tacatctatt       420
ttattctatt ttagcctcta aattaagaaa actaaaactc tattttagtt tttttattta    480
ataatttaga tataaaatag aataaaataa agtgactaaa aattaaacaa ataccctta     540
agaaattaaa aaactaagg aaacatttt cttgtttcga gtagataatg ccagcctgtt      600
aaacgccgtc gacgagtcta acggacacca accagcgaac cagcagcgtc gcgtcgggcc    660
aagcgaagca gacggcacgg catctctgtc gctgcctctg gaccctctc gagagttccg     720
ctccaccgtt ggacttgctc cgctgtcggc atccagaaat tgcgtggcgg agcggcagac    780
gtgagccggc acggcaggcg gcctcctcct cctctcacgg caccggcagc tacggggat    840
tcctttccca ccgctccttc gctttccctt ctcgcccgc cgtaataaat agacacccc     900
tccacaccct ctttccccaa cctcgtgttg ttcggagcgc acacacacac aaccagatct   960
cccccaaatc cacccgtcgg cacctccgct tcaaggtacg ccgctcgtcc tcccccccc    1020
ccctctcta ccttctctag atcggcgttc cggtccatgg ttagggcccg gtagttctac    1080
ttctgttcat gtttgtgtta gatccgtgtt tgtgttagat ccgtgctgct agcgttcgta   1140
cacggatgcg aacctgtacgt cagacacgtt ctgattgcta acttgccagt gtttctcttt   1200
ggggaatcct gggatggctc tagccgttcc gcagacggga tcgatttcat gatttttttt   1260
gtttcgttgc atagggtttg gtttgccctt ttcctttatt tcaatatatg ccgtgcactt   1320
gtttgtcggg tcatcttttc atgctttttt ttgtcttggt tgtgatgatg tggtctggtt   1380
gggcggtcgt tctagatcgg agtagaattc tgtttcaaac tacctggtgg atttattaat   1440
tttggatctg tatgtgtgtg ccatacatat tcatagttac gaattgaaga tgatggatgg   1500
aaatatcgat ctaggatagg tatacatgtt gatgcgggtt ttactgatgc atatacagag   1560
atgcttttg ttcgcttggt tgtgatgatg tggtgtggtt gggcggtcgt tcattcgttc    1620
tagatcggag tagaatactg tttcaaacta cctggtgtat ttattaattt tggaactgta    1680
tgtgtgtgtc atacatcttc atagttacga gtttaagatg gatggaaata tcgatctagg   1740
ataggtatac atgttgatgt gggttttact gatgcatata catgatgcca tatgcagcat   1800
ctattcatat gctctaacct tgagtaccta tctattataa taaacaagta tgttttataa   1860
ttattttgat cttgatatac ttggatgatg gcatatgcag cagctatatg tggatttttt   1920
tagccctgcc ttcatacgct atttatttgc ttggtactgt ttcttttgtc gatgctcacc   1980
ctgttgtttg tgttacttc tgcagggatc cccgatcatg caaaaactca ttaactcagt    2040
gcaaaactat gcctggggca gcaaaacggc gttgactgaa ctttatggta tggaaaatcc   2100
gtccagccag ccgatggccg agctgtggat gggcgcacat ccgaaaagca gttcacgagt   2160
gcagaatgcc gccggagata tcgtttcact gcgtgatgtg attgagagtg ataaatcgac   2220
tctgctcgga gaggccgttg ccaaacgctt tggcgaactg cctttcctgt tcaaagtatt   2280
atgcgcagca cagccactct ccattcaggt tcatccaaac aaacacaatt ctgaaatcgg   2340
ttttgccaaa gaaatgccg caggtatccc gatggatgcc gccgagcgta actataaaga   2400
tcctaaccac aagccggagc tggttttgc gctgacgcct tccttgcga tgaacgcgtt    2460
```

-continued

```
tcgtgaattt tccgagattg tctccctact ccagccggtc gcaggtgcac atccggcgat   2520
tgctcacttt ttacaacagc ctgatgccga acgtttaagc gaactgttcg ccagcctgtt   2580
gaatatgcag ggtgaagaaa atcccgcgc gctggcgatt ttaaaatcgg ccctcgatag   2640
ccagcagggt gaaccgtggc aaacgattcg tttaatttct gaattttacc cggaagacag   2700
cggtctgttc tccccgctat tgctgaatgt ggtgaaattg aaccctggcg aagcgatgtt   2760
cctgttcgct gaaacaccgc acgcttacct gcaaggcgtg gcgctggaag tgatggcaaa   2820
ctccgataac gtgctgcgtg cgggtctgac gcctaaatac attgatattc cggaactggt   2880
tgccaatgtg aaattcgaag ccaaaccggc taaccagttg ttgacccagc cggtgaaaca   2940
aggtgcagaa ctggacttcc cgattccagt ggatgatttt gccttctcgc tgcatgacct   3000
tagtgataaa gaaaccacca ttagccagca gagtgccgcc attttgttct gcgtcgaagg   3060
cgatgcaacg ttgtggaaag gttctcagca gttacagctt aaaccgggtg aatcagcgtt   3120
tattgccgcc aacgaatcac cggtgactgt caaaggccac ggccgtttag cgcgtgttta   3180
caacaagctg taagagctta ctgaaaaaat taacatctct tgctaagctg ggagctctag   3240
atctgttctg cacaaagtgg agtagtcagt catcgatcag gaaccagaca ccagactttt   3300
attcatacag tgaagtgaag tgaagtgcag tgcagtgagt tgctggtttt tgtacaactt   3360
agtatgtatt tgtatttgta aaatacttct atcaataaaa tttctaattc ctaaaaccaa   3420
aatccagtgg gtaccgaatt cactggccgt cgttttacaa cgtcgtgact gggaaaaccc   3480
tggcgttacc caacttaatc gccttgcagc acatccccct ttcgccagct ggcgtaatag   3540
cgaagaggcc cgcaccgatc gcccttccca acagttgcgc agcctgaatg gcgaatggcg   3600
cctgatgcgg tattttctcc ttacgcatct gtgcggtatt tcacaccgca tatggtgcac   3660
tctcagtaca atctgctctg atgccgcata gttaagccag ccccgacacc cgccaacacc   3720
cgctgacgcg ccctgacggg cttgtctgct cccggcatcc gcttacagac aagctgtgac   3780
cgtctccggg agctgcatgt gtcagaggtt ttcaccgtca tcaccgaaac gcgcgagacg   3840
aaagggcctc gtgatacgcc tatttttata ggttaatgtc atgataataa tggtttctta   3900
gacgtcaggt ggcactttc ggggaaatgt gcgcggaacc cctatttgtt tattttcta    3960 aatacattca aatatgtatc cgctcatgag acaataaccc tgataaatgc ttcaatggcg   4020
cgccgcggcc gcttaagaat attgaaaaag gaagagtatg agtattcaac atttccgtgt   4080
cgcccttatt ccctttttg cggcattttg ccttcctgtt tttgctcacc cagaaacgct   4140
ggtgaaagta aaagatgctg aagatcagtt gggtgcacga gtgggttaca tcgaactgga   4200
tctcaacagc ggtaagatcc ttgagagttt tcgccccgaa gaacgttttc caatgatgag   4260
cacttttaaa gttctgctat gtggcgcggt attatcccgt attgacgccg ggcaagagca   4320
actcggtcgc cgcatacact attctcagaa tgacttggtt gagtactcac cagtcacaga   4380
aaagcatctt acgatggca tgacagtaag agaattatgc agtgctgcca taaccatgag   4440
tgataacact gcggccaact tacttctgac aacgatcgga ggaccgaagg agctaaccgc   4500
ttttttgcac aacatggggg atcatgtaac tcgccttgat cgttgggaac cggagctgaa   4560
tgaagccata ccaaacgacg agcgtgacac cacgatgcct gtagcaatgg caacaacgtt   4620
gcgcaaacta ttaactggcg aactacttac tctagcttcc cggcaacaat taatagactg   4680
gatggaggcg gataaagttg caggaccact tctgcgctcg gcccttccgg ctggctggtt   4740
tattgctgat aaatctggag ccggtgagcg tgggtctcgc ggtatcattg cagcactggg   4800
gccagatggt aagccctccc gtatcgtagt tatctacacg acggggagtc aggcaactat   4860
```

-continued

```
ggatgaacga aatagacaga tcgctgagat aggtgcctca ctgattaagc attggtaact    4920
gtcagaccaa gtttactcat atatacttta gattgattta aaacttcatt tttaatttaa    4980
aaggatctag gtgaagatcc ttttttgataa tctcatgacc aaaatccctt aacgtgagtt   5040
tcgttccac tgagcgtcag accccgtaga aaagatcaaa ggatcttctt gagatccttt     5100
ttttctgcgc gtaatctgct gcttgcaaac aaaaaaacca ccgctaccag cggtggtttg    5160
tttgccggat caagagctac caactctttt tccgaaggta actggcttca gcagagcgca    5220
gataccaaat actgtccttc tagtgtagcc gtagttaggc caccacttca agaactctgt    5280
agcaccgcct acatacctcg ctctgctaat cctgttacca gtggctgctg ccagtggcga    5340
taagtcgtgt cttaccgggt tggactcaag acgatagtta ccggataagg cgcagcggtc    5400
gggctgaacg gggggttcgt gcacacagcc cagcttggag cgaacgacct acaccgaact    5460
gagataccta cagcgtgagc tatgagaaag cgccacgctt cccgaaggga gaaaggcgga    5520
caggtatccg gtaagcggca gggtcggaac aggagagcgc acgagggagc ttccaggggg    5580
aaacgcctgg tatctttata gtcctgtcgg gtttcgccac ctctgacttg agcgtcgatt    5640
tttgtgatgc tcgtcagggg ggcggagcct atggaaaaac gccagcaacg cggcctttt    5700
acggttcctg gccttttgct ggccttttgc tcacatgttc tttcctgcgt tatcccctga    5760
ttctgtggat aaccgtatta ccgcctttga gtgagctgat accgctcgcc gcagccgaac    5820
gaccgagcgc agcgagtcag tgagcgagga agcggaagag cttaagcggc gcggcgcgc    5880
cgcccaatac gcaaaccgcc tctccccgcg cgttggccga ttcattaatg cagctggcac    5940
gacaggtttc ccgactggaa agcgggcagt gagcgcaacg caattaatgt gagttagctc    6000
actcattagg caccccaggc tttacacttt atgcttccgg ctcgtatgtt gtgtggaatt    6060
gtgagcggat aacaatttca cacaggaaac agctatgacc atgattacgc c             6111
```

<210> SEQ ID NO 10
<211> LENGTH: 13737
<212> TYPE: DNA
<213> ORGANISM: Plasmid
<220> FEATURE:
<223> OTHER INFORMATION: Description of Artificial Sequence:Plasmid
<400> SEQUENCE: 10

```
gatccagaat tcgtgatcaa atggccgcaa caagcagcac aagcagccag tctttttgaca     60
tagagctcga catcatcggc cagcaaccgc ctcttctttc aatctacacc cagatcagtc    120
tcgtttaccc cgtctctgat ccctcccagt atcccaccat cgtcagcacc cttgaggaag    180
gcctaaaacg cctctctcaa accttcccat gggtcgcggg ccaggtcaag accgagggca    240
tcagcgaagg aaacacagga acttccaaga tcattccata tgaggagaca ccccgtcttg    300
tggtgaaaga cctccgtgat gattcctcag cgccaacgat cgaggggttg agaaaggcgg    360
gtttccccctt agagatgttt gacgagaacg tcgtcgctcc gaggaagaca ttagctatcg    420
gacctggcaa tggccccaac gacccgaagc ctgtgttgct attgcagctc aacttcatta    480
agggcggact cattctcacc gtcaacggac aacatggtgc tatggacatg acaggacaag    540
atgcaattat tcgtcttctc tccaaggcgt gccgcaacga atcattcacc gaggaggaaa    600
tctcggccat gaacctcgat cgcaagacgg tagtccctct ccttgaaaac tacaaagttg    660
gtcctgagct agaccaccag atcgccaaac ctgcgcctgc tggcgacgct ccacccgcac    720
cggccaaggc aagctgggcg ttcttttcat tcactcccaa ggccctctcg gagctgaaag    780
```

```
acgcagccac aaagactctt gacgcgtcgt ccaagtttgt gtcaactgat gatgctcttt    840
cggcgtttat ctggcaatca acctcgcgcg tacgtctcgc aagattggat gcttccacac    900
ctactgaatt ctgccgcgct gtcgacatgc ggggcccaat gggcgtatca agcacatacc    960
caggccttct tcaaaacatg acctaccatg actcgaccgt cgccgaaatc gccaacgaac   1020
cacttggcgc aacagcatca cgcctgcgct cggaactcaa cagtgatcgt ttgcgcagac   1080
gaacacaagc tttggcgacg tacatgcatg gcctgcctga caagtcgagc gtctccctga   1140
ccgccgatgc gaatccgtca agcagcatca tgctgagttc ctgggccaag gtgggatgct   1200
gggagtatga ctttgggttt ggactgggta agcctgagag tgtgagaaga cctcgctttg   1260
aaccttttga gagtttgatg tactttatgc ccaagaagcc tgatggggag tttacggcgt   1320
ccatttctct gagggatgag gatatggaga gactaaaggc ggatgaggag tggacaaagt   1380
acgcaaagta tattgggtag atagtttact agactactgc agggatatcg tggatccccc   1440
gaatttcccc gatcgttcaa acatttggca ataaagtttc ttaagattga atcctgttgc   1500
cggtcttgcg atgattatca tctaatttct gttgaattac gttaagcatg taataattaa   1560
catgtaatgc atgacgttat ttatgagatg ggtttttatg attagagtcc cgcaattata   1620
catttaatac gcgatagaaa acaaaatata gcgcgcaaac taggataaat tatcgcgcgc   1680
ggtgtcatct atgttactag atccgggaat tcggcgcgcc caattgattt aaatggccgc   1740
tgcggccaat tcctgcagcg ttgcggttct gtcagttcca aacgtaaaac ggcttgtccc   1800
gcgtcatcgg cggggtcat aacgtgactc ccttaattct ccgctcatga tcagattgtc   1860
gtttcccgcc ttcagtttaa actatcagtg tttgacagga tatattggcg ggtaaaccta   1920
agagaaaaga gcgtttatta gaataatcgg atatttaaaa gggcgtgaaa aggtttatcc   1980
gttcgtccat ttgtatgtgc atgccaacca cagggttccc cagatctggc gccggccagc   2040
gagacgagca agattggccg ccgcccgaaa cgatccgaca gcgcgcccag cacaggtgcg   2100
caggcaaatt gcaccaacgc atacagcgcc agcagaatgc catagtgggc ggtgacgtcg   2160
ttcgagtgaa ccagatcgcg caggaggccc ggcagcaccg gcataatcag gccgatgccg   2220
acagcgtcga gcgcgacagt gctcagaatt acgatcaggg gtatgttggg tttcacgtct   2280
ggcctccgga ccagcctccg ctggtccgat tgaacgcgcg gattctttat cactgataag   2340
ttggtggaca tattatgttt atcagtgata aagtgtcaag catgacaaag ttgcagccga   2400
atacagtgat ccgtgccgcc ctggacctgt tgaacgaggt cggcgtagac ggtctgacga   2460
cacgcaaact ggcggaacgg ttgggggttc agcagccggc gctttactgg cacttcagga   2520
acaagcgggc gctgctcgac gcactggccg aagccatgct ggcggagaat catacgcatt   2580
cggtgccgag agccgacgac gactggcgct catttctgat cgggaatgcc cgcagcttca   2640
ggcaggcgct gctcgcctac cgcgatggcg cgcgcatcca tgccggcacg cgaccgggcg   2700
caccgcagat ggaaacggcc gacgcgcagc ttcgcttcct ctgcgaggcg gttttcgg   2760
ccggggacgc cgtcaatgcg ctgatgacaa tcagctactt cactgttggg gccgtgcttg   2820
aggagcaggc cggcgacagc gatgccggcg agcgcggcgg caccgttgaa caggctccgc   2880
tctcgccgct gttgcgggcc gcgatagacg ccttcgacga agccggtccg gacgcagcgt   2940
tcgagcagga actcgcggtg attgtcgatg gattggcgaa aaggaggctc gttgtcagga   3000
acgttgaagg accgagaaag ggtgacgatt gatcaggacc gctgccggag cgcaacccac   3060
tcactacagc agagccatgt agacaacatc ccctcccccct ttccaccgcg tcagacgccc   3120
gtagcagccc gctacgggct ttttcatgcc ctgccctagc gtccaagcct cacggccgcg   3180
```

```
ctcggcctct ctggcggcct tctggcgctc ttccgcttcc tcgctcactg actcgctgcg   3240
ctcggtcgtt cggctgcggc gagcggtatc agctcactca aaggcggtaa tacggttatc   3300
cacagaatca gggataacg caggaaagaa catgtgagca aaaggccagc aaaaggccag   3360
gaaccgtaaa aaggccgcgt tgctggcgtt tttccatagg ctccgccccc ctgacgagca   3420
tcacaaaaat cgacgctcaa gtcagaggtg cgaaacccg acaggactat aaagatacca   3480
ggcgtttccc cctggaagct ccctcgtgcg ctctcctgtt ccgaccctgc cgcttaccgg   3540
atacctgtcc gcctttctcc cttcgggaag cgtggcgctt tccgctgca taaccctgct   3600
tcgggtcat tatagcgatt ttttcggtat atccatcctt tttcgcacga tatacaggat   3660
tttgccaaag ggttcgtgta gactttcctt ggtgtatcca acggcgtcag ccgggcagga   3720
taggtgaagt aggcccaccc gcgagcgggt gttccttctt cactgtccct tattcgcacc   3780
tggcggtgct caacgggaat cctgctctgc gaggctggcc ggctaccgcc ggcgtaacag   3840
atgagggcaa gcggatggct gatgaaacca agccaaccag gaagggcagc ccacctatca   3900
aggtgtactg ccttccagac gaacgaagag cgattgagga aaggcggcg gcggccggca   3960
tgagcctgtc ggcctacctg ctggccgtcg gccagggcta caaaatcacg ggcgtcgtgg   4020
actatgagca cgtccgcgag ctggcccgca tcaatggcga cctgggccgc ctgggcggcc   4080
tgctgaaact ctggctcacc gacgacccgc gcacggcgcg gttcggtgat gccacgatcc   4140
tcgccctgct ggcgaagatc gaagagaagc aggacgagct tggcaaggtc atgatgggcg   4200
tggtccgccc gagggcagag ccatgacttt tttagccgct aaaacggccg gggggtgcgc   4260
gtgattgcca agcacgtccc catgcgctcc atcaagaaga gcgacttcgc ggagctggtg   4320
aagtacatca ccgacgagca aggcaagacc gagcgccttt gcgacgctca ccgggctggt   4380
tgccctcgcc gctgggctgg cggccgtcta tggccctgca aacgcgccag aaacgccgtc   4440
gaagccgtgt gcgagacacc gcggccggcc gccggcgttg tggatacctc gcggaaaact   4500
tggccctcac tgacagatga ggggcggacg ttgacacttg aggggccgac tcacccggcg   4560
cggcgttgac agatgagggg caggctcgat ttcggccggc gacgtggagc tggccagcct   4620
cgcaaatcgg cgaaaacgcc tgattttacg cgagtttccc acagatgatg tggacaagcc   4680
tggggataag tgccctgcgg tattgacact tgaggggcgc gactactgac agatgagggg   4740
cgcgatcctt gacacttgag gggcagagtg ctgacagatg agggcgcac ctattgacat   4800
ttgagggct gtccacaggc agaaaatcca gcatttgcaa gggtttccgc ccgttttttcg   4860
gccaccgcta acctgtcttt taacctgctt ttaaaccaat atttataaac cttgttttta   4920
accagggctg cgccctgtgc gcgtgaccgc gcacgccgaa ggggggtgcc ccccttctc   4980
gaaccctccc ggcccgctaa cgcgggcctc ccatcccccc agggggctgcg cccctcggcc   5040
gcgaacggcc tcaccccaaa aatggcagcg ctggcagtcc ttgccattgc cgggatcggg   5100
gcagtaacgg gatgggcgat cagcccgagc gcgacgcccg gaagcattga cgtgccgcag   5160
gtgctggcat cgacattcag cgaccaggtg ccgggcagtg agggcggcgg cctggggtggc   5220
ggcctgccct tcacttcggc cgtcggggca ttcacggact tcatggcggg gccggcaatt   5280
tttaccttgg gcattcttgg catagtggtc gcgggtgccg tgctcgtgtt cggggggtgcg   5340
ataaacccag cgaaccattt gaggtgatag gtaagattat accgaggtat gaaaacgaga   5400
attggacctt tacagaatta ctctatgaag cgccatattt aaaaagctac caagacgaag   5460
aggatgaaga ggatgaggag gcagattgcc ttgaatatat tgcacaatact gataagataa   5520
```

```
tatatctttt atatagaaga tatcgccgta tgtaaggatt tcaggggggca aggcataggc    5580 agcgcgctta tcaatatatc tatagaatgg gcaaagcata aaaacttgca tggactaatg    5640
cttgaaaccc aggacaataa ccttatagct tgtaaattct atcataattg ggtaatgact    5700
ccaacttatt gatagtgttt tatgttcaga taatgcccga tgactttgtc atgcagctcc    5760
accgattttg agaacgacag cgacttccgt cccagccgtg ccaggtgctg cctcagattc    5820
aggttatgcc gctcaattcg ctgcgtatat cgcttgctga ttacgtgcag ctttcccttc    5880
aggcgggatt catacagcgg ccagccatcc gtcatccata tcaccacgtc aaagggtgac    5940
agcaggctca taagacgccc cagcgtcgcc atagtgcgtt caccgaatac gtgcgcaaca    6000
accgtcttcc ggagactgtc atacgcgtaa acagccagc gctggcgcga tttagccccg    6060
acatagcccc actgttcgtc catttccgcg cagacgatga cgtcactgcc cggctgtatg    6120
cgcgaggtta ccgactgcgg cctgagtttt ttaagtgacg taaaatcgtg ttgaggccaa    6180
cgcccataat gcgggctgtt gcccggcatc caacgccatt catggccata tcaatgattt    6240
tctggtgcgt accgggttga gaagcggtgt aagtgaactg cagttgccat gttttacggc    6300
agtgagagca gagatagcgc tgatgtccgg cggtgctttt gccgttacgc accaccccgt    6360
cagtagctga acaggaggga cagctgatag acacagaagc cactggagca cctcaaaaac    6420
accatcatac actaaatcag taagttggca gcatcaccca taattgtggt ttcaaaatcg    6480
gctccgtcga tactatgtta tacgccaact ttgaaaacaa ctttgaaaaa gctgttttct    6540
ggtatttaag gttttagaat gcaaggaaca gtgaattgga gttcgtcttg ttataattag    6600
cttcttgggg tatctttaaa tactgtagaa agaggaagg aataataaa tggctaaaat    6660 gagaatatca ccggaattga aaaaactgat cgaaaaatac cgctgcgtaa aagatacgga    6720
aggaatgtct cctgctaagg tatataagct ggtgggagaa aatgaaaacc tatatttaaa    6780
aatgacggac agccggtata aagggaccac ctatgatgtg gaacgggaaa aggacatgat    6840
gctatggctg gaaggaaagc tgcctgttcc aaaggtcctg cactttgaac ggcatgatgg    6900
ctggagcaat ctgctcatga gtgaggccga tggcgtcctt tgctcggaag agtatgaaga    6960
tgaacaaagc cctgaaaaga ttatcgagct gtatgcggag tgcatcaggc tctttcactc    7020
catcgacata tcggattgtc cctatacgaa tagcttagac agccgcttag ccgaattgga    7080
ttacttactg aataacgatc tggccgatgt ggattgcgaa aactgggaag aagacactcc    7140
atttaaagat ccgcgcgagc tgtatgattt tttaaagacg gaaaagcccg aagaggaact    7200
tgtcttttcc cacggcgacc tgggagacag caacatcttt gtgaaagatg gcaaagtaag    7260
tggctttatt gatcttggga gaagcggcag ggcggacaag tggtatgaca ttgccttctg    7320
cgtccggtcg atcagggagg atatcgggga agaacagtat gtcgagctat tttttgactt    7380
actggggatc aagcctgatt gggagaaaat aaaatattat atttactgg atgaattgtt    7440 ttagtaccta gatgtggcgc aacgatgccg gcgacaagca ggagcgcacc gacttcttcc    7500
gcatcaagtg ttttggctct caggccgagg cccacggcaa gtatttgggc aagggtcgc    7560 tggtattcgt gcagggcaag attcggaata ccaagtacga aaggacggc cagacggtct    7620 acgggaccga cttcattgcc gataaggtgg attatctgga caccaaggca ccaggcgggt    7680
caaatcagga ataagggcac attgccccgg cgtgagtcgg ggcaatcccg caaggagggt    7740
gaatgaatcg gacgtttgac cggaaggcat acaggcaaga actgatcgac gcggggtttt    7800
ccgccgagga tgccgaaacc atcgcaagcc gcaccgtcat gcgtgcgccc cgcgaaacct    7860
tccagtccgt cggctcgatg gtccagcaag ctacggccaa gatcgagcgc gacagcgtgc    7920
```

```
aactggctcc ccctgccctg cccgcgccat cggccgccgt ggagcgttcg cgtcgtctcg    7980
aacaggaggc ggcaggtttg gcgaagtcga tgaccatcga cacgcgagga actatgacga    8040
ccaagaagcg aaaaaccgcc ggcgaggacc tggcaaaaca ggtcagcgag gccaagcagg    8100
ccgcgttgct gaaacacacg aagcagcaga tcaaggaaat gcagctttcc ttgttcgata    8160
ttgcgccgtg gccggacacg atgcgagcga tgccaaacga cacggcccgc tctgccctgt    8220
tcaccacgcg caacaagaaa atcccgcgcg aggcgctgca aaacaaggtc attttccacg    8280
tcaacaagga cgtgaagatc acctacaccg gcgtcgagct gcgggccgac gatgacgaac    8340
tggtgtggca gcaggtgttg gagtacgcga agcgcacccc tatcggcgag ccgatcacct    8400
tcacgttcta cgagctttgc caggacctgg gctggtcgat caatggccgg tattacacga    8460
aggccgagga atgcctgtcg cgcctacagg cgacggcgat gggcttcacg tccgaccgcg    8520
ttgggcacct ggaatcggtg tcgctgctgc accgcttccg cgtcctggac cgtggcaaga    8580
aaacgtcccg ttgccaggtc ctgatcgacg aggaaatcgt cgtgctgttt gctggcgacc    8640
actacacgaa attcatatgg gagaagtacc gcaagctgtc gccgacggcc cgacggatgt    8700
tcgactattt cagctcgcac cgggagccgt acccgctcaa gctggaaacc ttccgcctca    8760
tgtgcggatc ggattccacc cgcgtgaaga agtggcgcga gcaggtcggc gaagcctgcg    8820
aagagttgcg aggcagcggc ctggtggaac acgcctgggt caatgatgac ctggtgcatt    8880
gcaaacgcta gggccttgtg gggtcagttc cggctggggg ttcagcagcc agcgctttac    8940
tggcatttca ggaacaagcg ggcactgctc gacgcacttg cttcgctcag tatcgctcgg    9000
gacgcacggc gcgctctacg aactgccgat aaacagagga ttaaaattga caattgtgat    9060
taaggctcag attcgacggc ttggagcggc cgacgtgcag gatttccgcg agatccgatt    9120
gtcggccctg aagaaagctc cagagatgtt cgggtccgtt tacgagcacg aggagaaaaa    9180
gcccatggag gcgttcgctg aacggttgcg agatgccgtg gcattcggcg cctacatcga    9240
cggcgagatc attgggctgt cggtcttcaa acaggaggac ggccccaagg acgctcacaa    9300
ggcgcatctg tccggcgttt tcgtggagcc cgaacagcga ggccgagggg tcgccggtat    9360
gctgctgcgg gcgttgccgg cgggtttatt gctcgtgatg atcgtccgac agattccaac    9420
gggaatctgg tggatgcgca tcttcatcct cggcgcactt aatatttcgc tattctggag    9480
cttgttgttt atttcggtct accgcctgcc gggcgggtc gcggcgacgg taggcgctgt    9540
gcagccgctg atggtcgtgt tcatctctgc cgctctgcta ggtagcccga tacgattgat    9600
ggcggtcctg ggggctattt gcggaactgc gggcgtggcg ctgttggtgt tgacaccaaa    9660
cgcagcgcta gatcctgtcg gcgtcgcagc gggcctggcg ggggcggttt ccatggcgtt    9720
cggaaccgtg ctgacccgca agtggcaacc tcccgtgcct ctgctcacct ttaccgcctg    9780
gcaactggcg gccggaggac ttctgctcgt tccagtagct ttagtgtttg atccgccaat    9840
cccgatgcct acaggaacca atgttctcgg cctggcgtgg ctcggcctga tcggagcggg    9900
tttaacctac ttcctttggt tccgggggat ctcgcgactc gaacctacag ttgtttcctt    9960
actgggcttt ctcagccccca gatctgggt cgatcagccg gggatgcatc aggccgacag   10020
tcggaacttc gggtccccga cctgtaccat tcggtgagca atggataggg gagttgatat   10080
cgtcaacgtt cacttctaaa gaaatagcgc cactcagctt cctcagcggc tttatccagc   10140
gatttcctat tatgtcggca tagttctcaa gatcgacagc ctgtcacggt taagcgagaa   10200
atgaataaga aggctgataa ttcggatctc tgcgagggag atgatatttg atcacaggca   10260
```

```
gcaacgctct gtcatcgtta caatcaacat gctaccctcc gcgagatcat ccgtgtttca   10320
aacccggcag cttagttgcc gttcttccga atagcatcgg taacatgagc aaagtctgcc   10380
gccttacaac ggctctcccg ctgacgccgt cccggactga tgggctgcct gtatcgagtg   10440
gtgattttgt gccgagctgc cggtcgggga gctgttggct ggctggtggc aggatatatt   10500
gtggtgtaaa caaattgacg cttagacaac ttaataacac attgcggacg tttttaatgt   10560
actgcggtac ggccatgctg gccgcccggg caccggtaaa tttcctgcag ggctagcgaa   10620
ttcgagctcg gtaccctgg attttggttt taggaattag attattgata gaagtatttt    10680
acaaatacaa atacatacta agggtttctt atatgctcaa cacatgagcg aaaccctata   10740
agaaccctaa ttcccttatc tgggaactac tcacacatta ttatagagag agatagattt   10800
gtagagagag actggtgatt tcagcgggca tgcctgcagg tcgactcaga tctgggtaac   10860
tggcctaact ggccttggag gagctggcaa ctcaaaatcc ctttgccaaa aaccaacatc   10920
atgccatcca ccatgcttgt atccagctgc gcgcaatgta ccccgggctg tgtatcccaa   10980
agcctcatgc aacctaacag atggatcgtt tggaaggcct ataacagcaa ccacagactt   11040
aaaaccttgc gcctccatag acttaagcaa atgtgtgtac aatgtggatc ctaggcccaa   11100
cctttgatgc ctatgtgaca cgtaaacagt actctcaact gtccaatcgt aagcgttcct   11160
agccttccag ggcccagcgt aagcaatacc agccacaaca ccctcaacct cagcaaccaa   11220
ccaagggtat ctatcttgca acctctctag atcatcaatc cactcttgtg gtgtttgtgg   11280
ctctgtccta aagttcactg tagacgtctc aatgtaatgg ttaacgatat cacaaaccgc   11340
ggccatatca gctgctgtag ctggcctaat ctcaactggt ctcctctccg gagacatgtc   11400
gactctagag gatccccggg taccctgtcc tctccaaatg aaatgaactt ccttatatag   11460
aggaagggtc ttgcgaagga tagtgggatt gtgcgtcatc ccttacgtca gtggagatat   11520
cacatcaatc cacttgcttt gaagacgtgg ttggaacgtc ttcttttcc acgatgctcc    11580 tcgtgggtgg gggtccatct ttgggaccac tgtcggcaga ggcatcttca acgatggcct   11640
ttcctttatc gcaatgatgg catttgtagg agccaccttc cttttccact atcttcacaa   11700
taaagtgaca gatagctggg caatggaatc cgaggaggtt tccggatatt acccttttgtt  11760 gaaaagtctc aattgccctt tggtcttctg agactgtatc tttgatattt ttggagtaga   11820
caagcgtgtc gtgctccacc atgttgacga agatattctt cttgtcattg agtcgtaaga   11880
gactctgtat gaactgttcg ccagtcttta cggcgagttc tgttggtcct ctatttgaat   11940
ctttgactcc atgggaattg agatctctcg aggtttaaac gggccacgcc tgcggccgcc   12000
tcgaggtacc ggatttggag ccaagtctca taaacgccat tgtggaagaa agtcttgagt   12060
tggtggtaat gtaacagagt agtaagaaca gagaagagag agagtgtgag atacatgaat   12120
tgtcgggcaa caaaaatcct gaacatctta ttttagcaaa gagaaagagt tccgagtctg   12180
tagcagaaga gtgaggagaa atttaagctc ttggacttgt gaattgttcc gcctcttgaa   12240
tacttcttca atcctcatat attcttcttc tatgttacct gaaaccggc atttaatctc    12300 gcgggtttat tccggttcaa cattttttt gttttgagtt attatctggg cttaataacg    12360
caggcctgaa ataaattcaa ggcccaactg tttttttttt taagaagttg ctgttaaaaa   12420
aaaaaaaagg gaattaacaa caacaacaaa aaagataaa gaaataata acaattactt     12480 taattgtaga ctaaaaaaac atagatttta tcatgaaaaa aagagaaaag aaataaaac    12540 ttggatcaaa aaaaaaaaca tacagatctt ctaattatta acttttctta aaattaggt    12600 ccttttttccc aacaattagg tttagagttt tggaattaaa ccaaaaagat tgttctaaaa  12660
```

-continued

```
aatactcaaa tttggtagat aagtttcctt attttaatta gtcaatggta gatactttt    12720
tttcttttct ttattagagt agattagaat cttttatgcc aagttttgat aaattaaatc    12780
aagaagataa actatcataa tcaacatgaa attaaaagaa aaatctcata tatagtatta    12840
gtattctcta tatatattat gattgcttat tcttaatggg ttgggttaac caagacatag    12900
tcttaatgga aagaatcttt tttgaacttt ttccttattg attaaattct tctatagaaa    12960
agaaagaaat tatttgagga aagtatata caaaagaaa aatagaaaaa tgtcagtgaa    13020
gcagatgtaa tggatgacct aatccaacca ccaccatagg atgtttctac ttgagtcggt    13080
cttttaaaaa cgcacggtgg aaaatatgac acgtatcata tgattccttc ctttagtttc    13140
gtgataataa tcctcaactg atatcttcct ttttttgttt tggctaaaga tattttattc    13200
tcattaatag aaaagacggt tttgggcttt tggtttgcga tataaagaag accttcgtgt    13260
ggaagataat aattcatcct ttcgtctttt tctgactctt caatctctcc caaagcctaa    13320
agcgatctct gcaaatctct cgcgactctc tctttcaagg tatattttct gattcttttt    13380
gttttttgatt cgtatctgat ctccaatttt tgttatgtgg attattgaat cttttgtata    13440
aattgctttt gacaatattg ttcgtttcgt caatccagct tctaaatttt gtcctgatta    13500
ctaagatatc gattcgtagt gtttacatct gtgtaatttc ttgcttgatt gtgaaattag    13560
gattttcaag gacgatctat tcaatttttg tgttttcttt gttcgattct ctctgttta    13620
ggtttcttat gtttagatcc gtttctcttt ggtgttgttt tgatttctct tacggctttt    13680
gatttggtat atgttcgctg attggtttct acttgttcta ttgttttatt tcaggtg       13737
```

<210> SEQ ID NO 11
<211> LENGTH: 12949
<212> TYPE: DNA
<213> ORGANISM: Plasmid

<400> SEQUENCE: 11

```
agcttgcatg cctgcagtgc agcgtgaccc ggtcgtgccc ctctctagag ataatgagca      60
ttgcatgtct aagttataaa aaattaccac atatttttt tgtcacactt gtttgaagtg     120
cagtttatct atctttatac atatatttaa actttactct acgaataata taatctatag     180
tactacaata atatcagtgt tttagagaat catataaatg aacagttaga catggtctaa     240
aggacaattg agtattttga caacaggact ctacagtttt atcttttag tgtgcatgtg     300
ttctcctttt tttttgcaaa tagcttcacc tatataatac ttcatccatt ttattagtac     360
atccatttag ggtttagggt taatggtttt tatagactaa tttttttagt acatctattt     420
tattctattt tagcctctaa attaagaaaa ctaaaactct attttagttt ttttatttaa     480
taatttagat ataaaataga ataaaataaa gtgactaaaa attaaacaaa tacccttaa     540
gaaattaaaa aaactaagga aacattttc ttgtttcgag tagataatgc cagcctgtta     600
aacgccgtcg acgagtctaa cggacaccaa ccagcgaacc agcagcgtcg cgtcgggcca     660
agcgaagcag acggcacggc atctctgtcg ctgcctctgg accctctcg agagttccgc     720
tccaccgttg gacttgctcc gctgtcggca tccagaaatt gcgtggcgga gcggcagacg     780
tgagccggca cggcaggcgg cctcctcctc ctctcacggc accggcagct acgggggatt     840
ccttccccac cgctccttcg ctttcccttc ctcgcccgcc gtaataaata gacacccct      900
ccacacctc tttccccaac ctcgtgttgt tcggagcgca cacacacaca accagatctc     960
ccccaaatcc acccgtcggc acctccgctt caaggtacgc cgctcgtcct cccccccccc    1020
```

```
ccctctctac cttctctaga tcggcgttcc ggtccatggt tagggcccgg tagttctact      1080
tctgttcatg tttgtgttag atccgtgttt gtgttagatc cgtgctgcta gcgttcgtac      1140
acggatgcga cctgtacgtc agacacgttc tgattgctaa cttgccagtg tttctctttg      1200
gggaatcctg ggatggctct agccgttccg cagacgggat cgatttcatg atttttttg      1260 tttcgttgca tagggtttgg tttgcccttt tcctttattt caatatatgc cgtgcacttg      1320
tttgtcgggt catcttttca tgctttttt tgtcttggtt gtgatgatgt ggtctggttg      1380
ggcggtcgtt ctagatcgga gtagaattct gtttcaaact acctggtgga tttattaatt      1440
ttggatctgt atgtgtgtgc catacatatt catagttacg aattgaagat gatggatgga      1500
aatatcgatc taggataggt atacatgttg atgcgggttt tactgatgca tatacagaga      1560 tgcttttttgt tcgcttggtt gtgatgatgt ggtgtggttg ggcggtcgtt cattcgttct      1620
agatcggagt agaatactgt ttcaaactac ctggtgtatt tattaattt ggaactgtat       1680 gtgtgtgtca tacatcttca tagttacgag tttaagatgg atggaaatat cgatctagga      1740
taggtataca tgttgatgtg ggttttactg atgcatatac atgatggcat atgcagcatc      1800
tattcatatg ctctaacctt gagtacctat ctattataat aaacaagtat gttttataat      1860
tattttgatc ttgatatact tggatgatgg catatgcagc agctatatgt ggattttttt      1920
agccctgcct tcatacgcta tttatttgct tggtactgtt tcttttgtcg atgctcaccc      1980
tgttgtttgg tgttacttct gcagggatcc ccgatcatgc aaaaactcat taactcagtg      2040
caaaactatg cctggggcag caaaacggcg ttgactgaac tttatggtat ggaaaatccg      2100
tccagccagc cgatggccga gctgtggatg ggcgcacatc cgaaaagcag ttcacgagtg      2160
cagaatgccg ccggagatat cgtttcactg cgtgatgtga ttgagagtga taaatcgact      2220
ctgctcggag aggccgttgc caaacgcttt ggcgaactgc ctttcctgtt caaagtatta      2280
tgcgcagcac agccactctc cattcaggtt catccaaaca aacacaattc tgaaatcggt      2340
tttgccaaag aaaatgccgc aggtatcccg atggatgccg ccgagcgtaa ctataaagat      2400
cctaaccaca agccggagct ggtttttgcg ctgacgcctt tccttgcgat gaacgcgttt      2460
cgtgaatttt ccgagattgt ctccctactc cagccggtcg caggtgcaca tccggcgatt      2520
gctcactttt tacaacagcc tgatgccgaa cgtttaagcg aactgttcgc cagcctgttg      2580
aatatgcagg gtgaagaaaa atcccgcgcg ctggcgattt taaaatcggc cctcgatagc      2640
cagcagggtg aaccgtggca aacgattcgt ttaatttctg aatttacccc ggaagacagc      2700
ggtctgttct ccccgctatt gctgaatgtg gtgaaattga accctggcga agcgatgttc      2760
ctgttcgctg aaaacaccgca cgcttacctg caaggcgtgg cgctggaagt gatggcaaac      2820
tccgataacg tgctgcgtgc gggtctgacg cctaaataca ttgatattcc ggaactggtt      2880
gccaatgtga aattcgaagc caaaccggct aaccagttgt tgacccagcc ggtgaaacaa      2940
ggtgcagaac tggacttccc gattccagtg gatgattttg ccttctcgct gcatgacctt      3000
agtgataaag aaaccaccat tagccagcag agtgccgcca ttttgttctg cgtcgaaggc      3060
gatgcaacgt tgtggaaagg ttctcagcag ttacagctta aaccgggtga atcagcgttt      3120
attgccgcca acgaatcacc ggtgactgtc aaaggccacg gccgtttagc gcgtgtttac      3180
aacaagctgt aagagcttac tgaaaaaatt aacatctctt gctaagctgg gagctcgatc      3240
cgtcgacctg cagatcgttc aaacatttgg caataaagtt tcttaagatt gaatcctgtt      3300
gccggtcttg cgatgattat catataattt ctgttgaatt acgttaagca tgtaataatt      3360
aacatgtaat gcatgacgtt atttatgaga tgggttttta tgattagagt cccgcaatta      3420
```

-continued

```
tacatttaat acgcgataga aaacaaaata tagcgcgcaa actaggataa attatcgcgc   3480
gcggtgtcat ctatgttact agatctgcta gccctgcagg aaatttaccg gtgcccgggc   3540
ggccagcatg gccgtatccg caatgtgtta ttaagttgtc taagcgtcaa tttgtttaca   3600
ccacaatata tcctgccacc agccagccaa cagctccccg accggcagct cggcacaaaa   3660
tcaccactcg ataacaggcag cccatcagaa ttaattctca tgtttgacag cttatcatcg   3720
actgcacggt gcaccaatgc ttctggcgtc aggcagccat cggaagctgt ggtatggctg   3780
tgcaggtcgt aaatcactgc ataattcgtg tcgctcaagg cgcactcccg ttctggataa   3840
tgttttttgc gccgacatca taacggttct ggcaaatatt ctgaaatgag ctgttgacaa   3900
ttaatcatcc ggctcgtata atgtgtggaa ttgtgagcgg ataacaattt cacacaggaa   3960
acagaccatg agggaagcgt tgatcgccga agtatcgact caactatcag aggtagttgg   4020
cgtcatcgag cgccatctcg aaccgacgtt gctggccgta catttgtacg gctccgcagt   4080
ggatggcggc ctgaagccac acagtgatat tgatttgctg gttacggtga ccgtaaggct   4140
tgatgaaaca acgcggcgag ctttgatcaa cgaccttttg gaaacttcgg cttcccctgg   4200
agagagcgag attctccgcg ctgtagaagt caccattgtt gtgcacgacg acatcattcc   4260
gtggcgttat ccagctaagc gcgaactgca atttggagaa tggcagcgca atgacattct   4320
tgcaggtatc ttcgagccag ccacgatcga cattgatctg ctatcttgc tgacaaaagc    4380 aagagaacat agcgttgcct tggtaggtcc agcggcggag gaactctttg atccggttcc   4440
tgaacaggat ctatttgagg cgctaaatga aaccttaacg ctatggaact cgccgcccga   4500
ctgggctggc gatgagcgaa atgtagtgct tacgttgtcc cgcatttggt acagcgcagt   4560
aaccggcaaa atcgcgccga aggatgtcgc tgccgactgg gcaatggagc gcctgccggc   4620
ccagtatcag cccgtcatac ttgaagctag gcaggcttat cttggacaag aagatcgctt   4680
ggcctcgcgc gcagatcagt tggaagaatt tgttcactac gtgaaaggcg agatcaccaa   4740
agtagtcggc aaataaagct ctagtggatc tccgtacccc cggggatct ggctcgcggc    4800 ggacgcacga cgccggggcg agaccatagg cgatctccta aatcaatagt agctgtaacc   4860
tcgaagcgtt tcacttgtaa caacgattga aattttttgt cataaaattg aaatacttgg   4920
ttcgcatttt tgtcatccgc ggtcagccgc aattctgacg aactgcccat ttagctggag   4980
atgattgtac atccttcacg tgaaaatttc tcaagcgctg tgaacaaggg ttcagatttt   5040
agattgaaag gtgagccgtt gaaacacgtt cttcttgtcg atgacgacgt cgctatgcgg   5100
catcttatta ttgaataccct tacgatccac gccttcaaag tgaccgcggt agccgacagc   5160
acccagttca caagagtact ctcttccgcg acgtgcgatg tcgtggttgt tgatctaaat   5220
ttaggtcgtg aagatgggct cgagatcgtt cgtaatctgg cggcaaagtc tgatattcca   5280
atcataatta tcagtggcga ccgccttgag gagacggata aagttgttgc actcgagcta   5340
ggagcaagtg attttatcgc taagccgttc agtatcagag agtttctagc acgcattcgg   5400
gttgccttgc gcgtgcgccc caacgttgtc cgctccaaag accgacggtc ttttttgtttt   5460 actgactgga cacttaatct caggcaacgt cgcttgatgt ccgaagctgg cggtgaggtg   5520
aaacttacgg caggtgagtt caatcttctc ctcgcgtttt tagagaaacc ccgcgacgtt   5580
ctatcgcgcg agcaacttct cattgccagt cgagtacgcg acgaggaggt ttatgacagg   5640
agtatagatg ttctcatttt gaggctgcgc cgcaaacttg aggcagatcc gtcaagccct   5700
caactgataa aaacagcaag aggtgccggt tatttctttg acgcggacgt gcaggtttcg   5760
```

```
cacgggggga cgatggcagc ctgagccaat tcccagatcc ccgaggaatc ggcgtgagcg    5820
gtcgcaaacc atccggcccg gtacaaatcg gcgcggcgct gggtgatgac ctggtggaga    5880
agttgaaggc cgcgcaggcc gcccagcggc aacgcatcga ggcagaagca cgccccggtg    5940
aatcgtggca agcggccgct gatcgaatcc gcaaagaatc ccggcaaccg ccggcagccg    6000
gtgcgccgtc gattaggaag ccgcccaagg gcgacgagca accagatttt ttcgttccga    6060
tgctctatga cgtgggcacc cgcgatagtc gcagcatcat ggacgtggcc gttttccgtc    6120
tgtcgaagcg tgaccgacga gctggcgagg tgatccgcta cgagcttcca gacgggcacg    6180
tagaggtttc gcagggccg gccggcatgg ccagtgtgtg ggattacgac ctggtactga    6240
tggcggtttc ccatctaacc gaatccatga accgataccg ggaagggaag ggagacaagc    6300
ccggccgcgt gttccgtcca cacgttgcgg acgtactcaa gttctgccgg cgagccgatg    6360
gcggaaagca gaaagacgac ctggtagaaa cctgcattcg gttaaacacc acgcacgttg    6420
ccatgcagcg tacgaagaag gccaagaacg gccgcctggt gacggtatcc gagggtgaag    6480
ccttgattag ccgctacaag atcgtaaaga gcgaaaccgg gcggccggag tacatcgaga    6540
tcgagctagc tgattggatg taccgcgaga tcacagaagg caagaacccg gacgtgctga    6600
cggttcaccc cgattacttt ttgatcgatc ccggcatcgg ccgttttctc taccgcctgg    6660
cacgccgcgc gcaggcaag gcagaagcca gatggttgtt caagacgatc tacgaacgca    6720
gtggcagcgc cggagagttc aagaagttct gtttcaccgt gcgcaagctg atcgggtcaa    6780
atgacctgcc ggagtacgat ttgaaggagg aggcggggca ggctggcccg atcctagtca    6840
tgcgctaccg caacctgatc gagggcgaag catccgccgg ttcctaatgt acggagcaga    6900
tgctagggca aattgcccta gcaggggaaa aaggtcgaaa aggtctcttt cctgtggata    6960
gcacgtacat tgggaaccca aagccgtaca ttgggaaccg gaacccgtac attgggaacc    7020
caaagccgta cattgggaac cggtcacaca tgtaagtgac tgatataaaa gagaaaaaag    7080
gcgattttc cgcctaaaac tctttaaaac ttattaaaac tcttaaaacc cgcctggcct    7140
gtgcataact gtctggccag cgcacagccg aagagctgca aaaagcgcct acccttcggt    7200
cgctgcgctc cctacgcccc gccgcttcgc gtcggcctat cgcggccgct ggccgctcaa    7260
aaatggctgg cctacggcca ggcaatctac cagggcgcgg acaagccgcg ccgtcgccac    7320
tcgaccgccg gcgctgaggt ctgcctcgtg aagaaggtgt tgctgactca taccaggcct    7380
gaatcgcccc atcatccagc cagaaagtga gggagccacg gttgatgaga gctttgttgt    7440
aggtggacca gttggtgatt tgaactttt gctttgccac ggaacggtct gcgttgtcgg    7500
gaagatgcgt gatctgatcc ttcaactcag caaaagttcg atttattcaa caaagccgcc    7560
gtcccgtcaa gtcagcgtaa tgctctgcca gtgttacaac caattaacca attctgatta    7620
gaaaaactca tcgagcatca aatgaaactg caatttattc atatcaggat tatcaatacc    7680
atattttga aaaagccgtt tctgtaatga aggagaaaac tcaccgaggc agttccatag    7740
gatggcaaga tcctggtatc ggtctgcgat tccgactcgt ccaacatcaa tacaacctat    7800
taatttcccc tcgtcaaaaa taaggttatc aagtgagaaa tcaccatgag tgacgactga    7860
atccggtgag aatggcaaaa gctctgcatt aatgaatcgg ccaacgcgcg gggagaggcg    7920
gtttgcgtat tgggcgctct tccgcttcct cgctcactga ctcgctgcgc tcggtcgttc    7980
ggctgcggcg agcggtatca gctcactcaa aggcggtaat acggttatcc acagaatcag    8040
gggataacgc aggaaagaac atgtgagcaa aaggccagca aaaggccagg aaccgtaaaa    8100
aggccgcgtt gctggcgttt ttccataggc tccgcccccc tgacgagcat cacaaaaatc    8160
```

-continued

```
gacgctcaag tcagaggtgg cgaaacccga caggactata agataccag gcgtttcccc    8220
ctggaagctc cctcgtgcgc tctcctgttc cgaccctgcc gcttaccgga tacctgtccg    8280
cctttctccc ttcgggaagc gtggcgcttt ctcatagctc acgctgtagg tatctcagtt    8340
cggtgtaggt cgttcgctcc aagctgggct gtgtgcacga accccccgtt cagcccgacc    8400
gctgcgcctt atccggtaac tatcgtcttg agtccaaccc ggtaagacac gacttatcgc    8460
cactggcagc agccactggt aacaggatta gcagagcgag gtatgtaggc ggtgctacag    8520
agttcttgaa gtggtggcct aactacggct acactagaag aacagtattt ggtatctgcg    8580
ctctgctgaa gccagttacc ttcggaaaaa gagttggtag ctcttgatcc ggcaaacaaa    8640
ccaccgctgg tagcggtggt ttttttgttt gcaagcagca gattacgcgc agaaaaaaag    8700
gatctcaaga agatcctttg atcttttcta cggggtctga cgctcagtgg aacgaaaact    8760
cacgttaagg gattttggtc atgagattat caaaaaggat cttcacctag atccttttga    8820
tccggaatta attcctgtgg ttggcatgca catacaaatg gacgaacgga taaaccttt    8880
cacgcccttt aaatatccg attattctaa taaacgctct tttctcttag gtttacccgc    8940
caatatatcc tgtcaaacac tgatagttta aactgaaggc gggaaacgac aatctgatca    9000
tgagcggaga attaagggag tcacgttatg accccccgcg atgacgcggg acaagccgtt    9060
ttacgtttgg aactgacaga accgcaacgc tgcaggaatt ggccgcagcg gccatttaaa    9120
tggtaccta attaacgtac gaagcttgca tgcacgcggt ctagagcggc cgcctcgagg    9180
tacccgggccc cccctcgagg tcgacggtat cgataagctt gcatgcctgc agtgcagcgt    9240
gacccggtcg tgcccctctc tagagataat gagcattgca tgtctaagtt ataaaaaatt    9300
accacatatt ttttttgtca cacttgtttg aagtgcagtt tatctatctt tatacatata    9360
tttaaacttt actctacgaa taatataatc tatagtacta caataatatc agtgttttag    9420
agaatcatat aaatgaacag ttagacatgg tctaaaggac aattgagtat tttgacaaca    9480
ggactctaca gttttatctt tttagtgtgc atgtgttctc cttttttttt gcaaatagct    9540
tcacctatat aatacttcat ccattttatt agtacatcca tttagggttt agggttaatg    9600
gtttttatag actaattttt ttagtacatc tattttattc tattttagcc tctaaattaa    9660
gaaaactaaa actctatttt agtttttta tttaataatt tagatataaa atagaataaa    9720
ataaagtgac taaaattaa acaaataccc tttaagaaat taaaaaaact aaggaaacat    9780
ttttcttgtt tcgagtagat aatgccagcc tgttaaacgc cgtcgacgag tctaacggac    9840
accaaccagc gaaccagcag cgtcgcgtcg ggccaagcga agcagacggc acggcatctc    9900
tgtcgctgcc tctggacccc tctcgagagt tccgctccac cgttggactt gctccgctgt    9960
cggcatccag aaattgcgtg cggagcggc agacgtgagc cggcacggca ggcggcctcc   10020
tcctcctctc acggcacggc agctacgggg gattcctttc ccaccgctcc ttcgctttcc   10080
cttcctcgcc cgccgtaata aatagacacc ccctccacac cctctttccc caacctcgtg   10140
ttgttcggag cgcacacaca cacaaccaga tctcccccaa atccaccccgt cggcacctcc   10200
gcttcaaggt acgccgctcg tcctcccccc cccccctct ctaccttctc tagatcggcg   10260
ttccggtcca tggttagggc ccggtagttc tacttctgtt catgtttgtg ttagatccgt   10320
gtttgtgtta gatccgtgct gctagcgttc gtacacggat gcgacctgta cgtcagacac   10380
gttctgattg ctaacttgcc agtgtttctc tttggggaat cctgggatgg ctctagccgt   10440
tccgcagacg ggatcgattt catgatttt tttgtttcgt tgcataggggt ttggtttgcc   10500
```

```
cttttcctttt atttcaatat atgccgtgca cttgtttgtc gggtcatctt ttcatgcttt    10560
tttttgtctt ggttgtgatg atgtggtctg gttgggcggt cgttctagat cggagtagaa    10620
ttctgtttca aactacctgg tggatttatt aattttggat ctgtatgtgt gtgccataca    10680
tattcatagt tacgaattga agatgatgga tggaaatatc gatctaggat aggtatacat    10740
gttgatgcgg gttttactga tgcatataca gagatgcttt ttgttcgctt ggttgtgatg    10800
atgtggtgtg gttgggcggt cgttcattcg ttctagatcg gagtagaata ctgtttcaaa    10860
ctacctggtg tatttattaa ttttggaact gtatgtgtgt gtcatacatc ttcatagtta    10920
cgagtttaag atggatggaa atatcgatct aggataggta tacatgttga tgtgggtttt    10980
actgatgcat atacatgatg gcatatgcag catctattca tatgctctaa ccttgagtac    11040
ctatctatta taataaacaa gtatgtttta taattatttt gatcttgata tacttggatg    11100
atggcatatg cagcagctat atgtggattt ttttagccct gccttcatac gctatttatt    11160
tgcttggtac tgtttctttt gtcgatgctc accctgttgt ttggtgttac ttctgcaggt    11220
cgactctaga ggatccagaa ttcgtgatca aatggccgca acaagcagca caagcagcca    11280
gtcttttgac atagagctcg acatcatcgg ccagcaaccg cctcttcttt caatctacac    11340
ccagatcagt ctcgtttacc ccgtctctga tccctcccag tatcccacca tcgtcagcac    11400
ccttgaggaa ggcctaaaac gcctctctca aaccttccca tgggtcgcgg gccaggtcaa    11460
gaccgagggc atcagcgaag gaaacacagg aacttccaag atcattccat atgaggagac    11520
accccgtctt gtggtgaaag acctccgtga tgattcctca cgccaacga tcgagggggtt    11580 gagaaaggcg ggtttcccct tagagatgtt tgacgagaac gtcgtcgctc cgaggaagac    11640
attagctatc ggacctggca atggccccaa cgacccgaag cctgtgttgc tattgcagct    11700
caacttcatt aagggcggac tcattctcac cgtcaacgga caacatggtg ctatggacat    11760
gacaggacaa gatgcaatta ttcgtcttct ctccaaggcg tgccgcaacg aatcattcac    11820
cgaggaggaa atctcggcca tgaacctcga tcgcaagacg gtagtccctc tccttgaaaa    11880
ctacaaagtt ggtcctgagc tagaccacca gatcgccaaa cctgcgcctg ctggcgacgc    11940
tccacccgca ccggccaagg caagctgggc gttcttttca ttcactccca aggccctctc    12000
ggagctgaaa gacgcagcca caaagactct tgacgcgtcg tccaagtttg tgtcaactga    12060
tgatgctctt tcggcgttta tctggcaatc aacctcgcgc gtacgtctcg caagattgga    12120
tgcttccaca cctactgaat tctgccgcgc tgtcgacatg cggggcccaa tgggcgtatc    12180
aagcacatac ccaggccttc ttcaaaacat gacctaccat gactcgaccg tcgccgaaat    12240
cgccaacgaa ccacttggcg caacagcatc acgcctgcgc tcggaactca acagtgatcg    12300
tttgcgcaga cgaacacaag cttttggcgac gtacatgcat ggcctgcctg acaagtcgag    12360
cgtctccctg accgccgatg cgaatccgtc aagcagcatc atgctgagtt cctgggccaa    12420
ggtgggatgc tgggagtatg actttgggtt tggactggga agcctgaga gtgtgagaag    12480 acctcgcttt gaacctttg agagtttgat gtactttatg cccaagaagc ctgatgggga    12540
gtttacggcg tccatttctc tgagggatga ggatatggag agactaaagg cggatgagga    12600
gtggacaaag tacgcaaagt atattgggta gatagtttac tagactactg caggatatcg    12660
tggatccccg aatttccccg atcgttcaaa catttggcaa taaagtttct taagattgaa    12720
tcctgttgcc ggtcttgcga tgattatcat ataatttctg ttgaattacg ttaagcatgt    12780
aataattaac atgtaatgca tgacgttatt tatgagatgg gttttttatga ttagagtccc    12840
```

```
gcaattatac atttaatacg cgatagaaaa caaaatatag cgcgcaaact aggataaatt    12900
atcgcgcgcg gtgtcatcta tgttactaga tcgggaattc ggcgcgcca              12949
```